United States Patent [19]
Usman et al.

[11] Patent Number: 6,117,657
[45] Date of Patent: *Sep. 12, 2000

[54] NON-NUCLEOTIDE CONTAINING ENZYMATIC NUCLEIC ACID

[75] Inventors: Nassim Usman, Boulder; Francine Wincott, Longmont; Jasenka Matulic-Adamic, Boulder; Leonid Beigelman, Longmont; Alex Karpeisky, Boulder, all of Colo.

[73] Assignee: Ribozyme Pharmaceuticals, Inc., Boulder, Colo.

[*] Notice: This patent is subject to a terminal disclaimer.

[21] Appl. No.: 09/182,975

[22] Filed: Oct. 29, 1998

Related U.S. Application Data

[63] Continuation of application No. 08/363,253, Dec. 23, 1994, Pat. No. 5,891,683, which is a continuation-in-part of application No. 08/233,748, Apr. 19, 1994, abandoned, which is a continuation-in-part of application No. 08/152,481, Nov. 12, 1993, abandoned, which is a continuation-in-part of application No. 08/116,177, Sep. 2, 1993, abandoned.

[51] Int. Cl.$^7$ .......................... C12P 19/34; C07H 21/02; C12Q 1/68; A01N 43/04
[52] U.S. Cl. .......................... 435/91.31; 435/6; 435/91.3; 536/22.1; 536/23.1; 536/25.3; 536/25.1; 536/25.31
[58] Field of Search .......................... 435/6, 91.3, 91.31; 536/22.1, 23.1, 25.1, 25.3, 25.31

[56] References Cited

U.S. PATENT DOCUMENTS

| | | | |
|---|---|---|---|
| 4,987,071 | 1/1991 | Cech et al. | 635/91.31 |
| 5,672,501 | 9/1997 | Matulic-Adamic et al. | 435/240.2 |
| 5,891,683 | 4/1999 | Usman et al. | 435/91.31 |

FOREIGN PATENT DOCUMENTS

| | | |
|---|---|---|
| 0 360 257 | 3/1990 | European Pat. Off. . |
| 0 519 463 | 12/1992 | European Pat. Off. . |
| 93/23569 | 11/1993 | WIPO . |
| 94/02595 | 2/1994 | WIPO . |

OTHER PUBLICATIONS

Robins et al. "Nucleic acid related compounds. 42. A general procedure for the efficient deoxygenation of secondary alcohols. Regiospecific and stereoselective conversion of ribonucleosides to 2'–deoxynucleosides" J. Am. Chem. Soc. vol. 105, pp. 4059–406 1983.

Kiso et al. "Acetonationof some pentoses with 2,2–dimethoxypropane–N–,N–dimethylformamide–p–toluenesulfonic acid" Carbohydrate Research, vol. 52, pp. 95–101 1976.

Takeshita et al. "Oligonucleotides containing synthetic abasic sites" The Journal of Biological Chemistry, vol. 262, pp. 10171–10179 1987.

Millican et al. "Synthesis and biophysical studies of short oligodeoxynucleotides with novel modifications: apossible approach to the problem of mixed base oligodeoxynucleotide synthesis" Nucleic Acids Research, vol. 12, pp. 7435–7453 1984.

Iyer et al. "Abasic oligodeoxyribonucleoside phosphorothioates: synthesis and evaluation as anti–HIV–1 agents" Nucleic acids Research, vol. 18, pp. 2855–2859 1990.

Brown et al., "Expression of the c–myb Proto–oncogene in Bovine Vascular Smooth Muscle Cells," *J. Biol. Chem.* 267:4625–4630 (1992).

Chowrira et al., *NAR* 20:2835 (1990).

Cload and Schepartz, "Polyether Tethered Oligonucleotide Probes," *J. Am. Chem. Soc.* 113:6324 (1991).

Collins and Olive, "Reaction Conditions and Kinetics of Self–Cleavage of a Ribozyme Derived From Neurospora VS RNA," *Biochemistry* 32:2795–2799 (1993).

Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353 (1990).

Ferentz and Verdine, Disulfied Cross–Linked Oligonucleotides, *J. Am. Chem. Soc.* 113:4000 (1991).

(List continued on next page.)

*Primary Examiner*—Jeziz Riley

[57] ABSTRACT

Enzymatic nucleic acid molecule containing one or more non-nucleotide mimetics, and having activity to cleave an RNA or DNA molecule.

13 Claims, 19 Drawing Sheets

OTHER PUBLICATIONS

Guerrier–Takada et al., "The RNA Moiety of Ribonuclease P Is the Catalytic Subunit of the Enzyme," *Cell* 35:849–857 (1983).

Hampel and Tritz, "Hairpin catalytic RNA model: evidence for helices and sequence requrement for substrate RNA," *Nucleic Acids Research* 18:299 (1990).

Hampel and Tritz, "RNA Catalytic Properties of the Minimum (–)s TRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

Iyer et al., "Abasic oligodeoxyribonucleoside phosphorothioates: Synthesis and evaluation as anti–HIV–1 agents," *Nucleic Acids Research* 18:2855–2859 (1990).

Jaschke et al., "Automated Incorporation of Polyethylene Glycol into Synthetic Oligonucleotides," *Tetrahedron Lett,* 34:301 (1993).

Jeffries and Symons, "A Catalytic 13–mer Ribozyme," *Nucleic Acids Research* 17:1371–1377 (1989).

Kiso et al., "Acetonation of some pentoses with 2,2–dimethoxypropane–N–N–dimethyl-formamide–p–toluenesulfonic acid," *Carbohydrate Research* 52:95–101 (1976).

Ma et al., "Design and Synthesis of RNA Miniduplexes via a Synthetic Linker Approach. 2. Generation of Covalently Closed, Double–Stranded Cyclic HIV–1 TAR RNA Analogs with High Tat–Binding Affinity," *Nucleic Acids Research* 21:2585 (1993).

Ma et al., "Design and Synthesis of RNA Miniduplexes via a Synthetic Linker Approach," *Biochemistry* 32:1751 (1993).

McCurdy et al., "Deoxyoligonucleotides with Inverted Polarity: Synthesis and Use in Triple–Helix Formation," *Nucleosides & Nucleotides* 10:287 (1991).

Millican et al., "Synthesis and biophysical studies of short oligodeoxynucleotides with novel modifications: A possible approach to the problem of mixed base oligodeoxynucleotide synthesis," *Nucleic Acids Research* 12:7435–7453 (1984).

Nielsen et al., "Sequence–Selective Recognition of DNA by Strand Displacement with a Thymine–Substituted Polyamide," *Science* 254:1497 (1991).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914 (1991).

Paolella et al., Nuclease Resistant Ribozymes with High Catalytic Activity *EMBO J.* 11:1913–1919 (1992).

Perreault et al., "Mixed Deoxyribo–and Ribo–Oligonucleotides with Catalytic Activity," *Nature* 344:565–567 (1990).

Perreault et al., "Relationship between 2'–Hydroxyls and Magnesium Binding in the Hammerhead RNA Domain: A Model for Ribozyme Catalysis," *Biochemistry* 30:4020–4025 (1991).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistance 2'–Modified Hammerhead Ribozymes," *Science* 253:314–317 (1991).

Richardson and Schepartz, "Tethered Oligonucleotide Probes. A Strategy for the Recognition of Structured RNA," *J. Am. Chem. Soc.* 113:5109 (1991).

Robins et al., "Nucleic acid related compounds. 42. A general procedure for the efficient deoxygenation of secondary alcohols. Regiospecific and stereoselective conversion of ribonucleosides to 2'–deoxynucleosides," *J. Am. Chem. Soc.* 105:4059–4406 (1983).

Rossi et al, "Ribozymes as Anti–HIV–1 Therapeutic Agents: Principles, Applications, and Problems," *Acids Research and Human Retroviruses* 8:183–189 (1992).

Salunkhe et al., "Control of Folding and Binding of Oligonucleotides by Use of a Nonnucleotide Linker," *J. Am. Chem. Soc.* 114:6324 (1992).

Sarver et al., "Catalytic RNAs (Ribozymes): A New Frontier in Biomedical Applications," *AIDS Res. Revs.* 2:259 (1992).

Saville and Collins, "A Site–Specific Self–Cleavage Reaction Performed by a Novel RNA In Neurospora Mitchondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Seela and Kaiser, "Oligodeoxyribonucleotides containing 1,3–propanediol as nucleoside substitute," *Nucleic Acids Research* 15:3113 (1990).

Seela and Kaiser, *Nucleic Acids Research* 18:6353 (1990).

Stull et al., *Pharm. Res.* 12:465 (1995).

Takeshita et al., "Oligodeoxynucleotides containing synthetic abasic sites," *The Journal of Biological Chemistry* 262:10171–10179 (1987).

Uhlenbeck, "A Small Catalytic Oligoribonucleotide," *Nature* 328:596–600 (1987).

Usman and Cedergren, "Exploiting the chemical synthesis of RNA," *TIBS* 17:334–339 (1992).

Usman et al., "Chemical modification of hammerhead ribozymes: Activity and nuclease resistance," *Nucl. Acid. Symp. Genes* 31:153–164 (1994).

Usman et al., "Automated Chemical Synthesis of Long Oligoribonucleotides Using 2'–O–Silylated Ribonucleoside 3'–O–Phosphoramidites on a Controlled–Pore Glass Support. Synthesis of a 43–Nucleotide Sequence Similar to the 3'–Half Molecule of an *Escherichia coli* Formylmethoionine tRNA," *J. Am. Chem. Soc.* 109:7845–7854 (1987).

Yang et al., "Minimum Ribonucleotide Requirement for Catalysis by the RNA Hammerhead Domain," *Biochemistry* 31:5005–5009 (1992).

Zuckerman et al., "Efficient Method for the Preparation of Peptoids [Oligo (N–Substituted Glycines)] by Submonomer Solid–Phase Synthesis," *J. Am. Chem. Soc.* 114:10464 (1992).

Reagents and Conditions: i) PhOC(S)-Cl/DMAP, ii) Bu3SnH/AIBN, iii) CF3COOH, DMT-Cl/Pyr, iv) Bu3SnH/Bz2O2, v) 2M NaOH/Pyr/MEOH, DMT-Cl/Pyr, vi) TBDMS-Cl/AgNO3, vii) P(OCE)(N-iPr2)Cl

NON-NUCLEOTIDE CONTAINING ENZYMATIC NUCLEIC ACID

This application is a continuation of Usman et al., U.S. Ser. No. 08/363,253, filed Dec. 23, 1994, now U.S. Pat. No. 5,891,683, which is a continuation-in-part of Usman et al., U.S. Ser. No. 08/233,748 filed Apr. 19, 1994 now abandoned, which is a continuation-in-part of Usman et al., U.S. Ser. No. 08/152,481, filed Nov. 12, 1993 now abandoned, which is a continuation-in-part of Usman, U.S. Ser. No. 08/116,177, filed Sep. 2, 1993 now abandoned, all entitled "Non-Nucleotide Containing Enzymatic Nucleic Acid" and all hereby incorporated by reference herein (including drawings).

BACKGROUND OF THE INVENTION

This invention relates to chemically synthesized non-nucleotide-containing enzymatic nucleic acid.

The following is a brief history of the discovery and activity of enzymatic RNA molecules or ribozymes. This history is not meant to be complete but is provided only for understanding of the invention that follows. This summary is not an admission that all of the work described below is prior art to the claimed invention.

Prior to the 1970s it was thought that all genes were direct linear representations of the proteins that they encoded. This simplistic view implied that all genes were like ticker tape messages, with each triplet of DNA "letters" representing one protein "word" in the translation. Protein synthesis occurred by first transcribing a gene from DNA into RNA (letter for letter) and then translating the RNA into protein (three letters at a time). In the mid 1970s it was discovered that some genes were not exact, linear representations of the proteins that they encode. These genes were found to contain interruptions in the coding sequence which were removed from, or "spliced out" of, the RNA before it became translated into protein. These interruptions in the coding sequence were given the name of intervening sequences (or introns) and the process of removing them from the RNA was termed splicing. At least three different mechanisms have been discovered for removing introns from RNA. Two of these splicing mechanisms involve the binding of multiple protein factors which then act to correctly cut and join the RNA. A third mechanism involves cutting and joining of the RNA by the intron itself, in what was the first discovery of catalytic RNA molecules.

Cech and colleagues were trying to understand how RNA splicing was accomplished in a single-celled pond organism called *Tetrahymena thermophila*. Cech proved that the intervening sequence RNA was acting as its own splicing factor to snip itself out of the surrounding RNA. Continuing studies in the early 1980's served to elucidate the complicated structure of the Tetrahymena intron and to decipher the mechanism by which self-splicing occurs. Many research groups helped to demonstrate that the specific folding of the Tetrahymena intron is critical for bringing together the parts of the RNA that will be cut and spliced. Even after splicing is complete, the released intron maintains its catalytic structure. As a consequence, the released intron is capable of carrying out additional cleavage and splicing reactions on itself (to form intron circles). By 1986, Cech was able to show that a shortened form of the Tetrahymena intron could carry out a variety of cuffing and joining reactions on other pieces of RNA. The demonstration proved that the Tetrahymena intron can act as a true enzyme: (i) each intron molecule was able to cut many substrate molecules while the intron molecule remained unchanged, and (ii) reactions were specific for RNA molecules that contained a unique sequence (CUCU) which allowed the intron to recognize and bind the RNA. Zaug and Cech coined the term "ribozyme" to describe any ribonucleic acid molecule that has enzyme-like properties.

Also in 1986, Cech showed that the RNA substrate sequence recognized by the Tetrahymena ribozyme could be changed by altering a sequence within the ribozyme itself. This property has led to the development of a number of site-specific ribozymes that have been individually designed to cleave at other RNA sequences.

The Tetrahymena intron is the most well-studied of what is now recognized as a large class of introns, Group I introns. The overall folded structure, including several sequence elements, is conserved among the Group I introns, as is the general mechanism of splicing. Like the Tetrahymena intron, some members of this class are catalytic, i.e., the intron itself is capable of the self-splicing reaction. Other Group I introns require additional (protein) factors, presumably to help the intron fold into and/or maintain its active structure.

Ribonuclease P (RNaseP) is an enzyme comprised of both RNA and protein components which are responsible for converting precursor tRNA molecules into their final form by trimming extra RNA off one of their ends. RNaseP activity has been found in all organisms tested. Sidney Altman and his colleagues showed that the RNA component of RNaseP is essential for its processing activity; however, they also showed that the protein component also was required for processing under their experimental conditions. After Cech's discovery of self-splicing by the Tetrahymena intron, the requirement for both protein and RNA components in RNaseP was reexamined. In 1983, Altman and Pace showed that the RNA was the enzymatic component of the RNaseP complex. This demonstrated that an RNA molecule was capable of acting as a true enzyme, processing numerous tRNA molecules without itself undergoing any change.

The folded structure of RNaseP RNA has been determined, and while the sequence is not strictly conserved between RNAs from different organisms, this higher order structure is. It is thought that the protein component of the RNaseP complex may serve to stabilize the folded RNA in vivo.

Symons and colleagues identified two examples of a self-cleaving RNA that differed from other forms of catalytic RNA already reported. Symons was studying the propagation of the avocado sunblotch viroid (ASV), an RNA virus that infects avocado plants. Symons demonstrated that as little as 55 nucleotides of the ASV RNA was capable of folding in such a way as to cut itself into two pieces. It is thought that in vivo self-cleavage of these RNAs is responsible for cutting the RNA into single genome-length pieces during viral propagation. Symons discovered that variations on the minimal catalytic sequence from ASV could be found in a number of other plant pathogenic RNAs as well. Comparison of these sequences' revealed a common structural design consisting of three stems and loops connected by a central loop containing many conserved (invariant from one RNA to the next) nucleotides. The predicted secondary structure for this catalytic RNA reminded the researchers of the head of a hammer; thus it was named as such.

Uhlenbeck was successful in separating the catalytic region of the ribozyme from that of the substrate. Thus, it became possible to assemble a hammerhead ribozyme from 2 (or 3) small synthetic RNAs. A 19-nucleotide catalytic region and a 24-nucleotide substrate were sufficient to support specific cleavage. The catalytic domain of numerous hammerhead ribozymes have now been studied by both the Uhlenbeck's and Symons' groups with regard to defining the nucleotides required for specific assembly and catalytic activity, and determining the rates of cleavage under various conditions.

Haseloff and Gerlach showed it was possible to divide the domains of the hammerhead ribozyme in a different manner. By doing so, they placed most of the required sequences in the strand that did not get cut (the ribozyme) and only a required UH where H=C, A, or U in the strand that did get cut (the substrate). This resulted in a catalytic ribozyme that could be designed to cleave any UH RNA sequence embedded within a longer "substrate recognition" sequence. The specific cleavage of a long mRNA, in a predictable manner using several such hammerhead ribozymes, was reported in 1988.

One plant pathogen RNA (from the negative strand of the tobacco ringspot virus) undergoes self-cleavage but cannot be folded into the consensus hammerhead structure described above. Bruening and colleagues have independently identified a 50-nucleotide catalytic domain for this RNA. In 1990, Hampel and Tritz succeeded in dividing the catalytic domain into two parts that could act as substrate and ribozyme in a multiple-turnover, cutting reaction. As with the hammerhead ribozyme, the catalytic portion contains most of the sequences required for catalytic activity, while only a short sequence (GUC in this case) is required in the target. Hampel and Tritz described the folded structure of this RNA as consisting of a single hairpin and coined the term "hairpin" ribozyme (Bruening and colleagues use the term "paperclip" for this ribozyme motif). Continuing experiments suggest an increasing number of similarities between the hairpin and hammerhead ribozymes in respect to both binding of target RNA and mechanism of cleavage.

Hepatitis Delta Virus (HDV) is a virus whose genome consists of single-stranded RNA. A small region (about 80 nucleotides) in both the genomic RNA, and in the complementary anti-genomic RNA, is sufficient to support self-cleavage. In 1991, Been and Perrotta proposed a secondary structure for the HDV RNAs that is conserved between the genomic and anti-genomic RNAs and is necessary for catalytic activity. Separation of the HDV RNA into "ribozyme" and "substrate" portions has recently been achieved by Been. Been has also succeeded in reducing the size of the HDV ribozyme to about 60 nucleotides.

Table I lists some of the characteristics of the ribozymes discussed above.

Eckstein et al., International Publication No. WO 92/07065; Perrault et al., Nature 1990, 344:565; Pieken et al., Science 1991, 253:314; Usman and Cedergren, *Trends in Biochem. Sci.* 1992, 17:334; and Rossi et al., International Publication No. WO 91/03162, describe various chemical modifications that can be made to the sugar moieties of enzymatic nucleic acid molecules.

Usman, et al., WO 93/15187 in discussing modified structures in ribozymes states:

It should be understood that the linkages between the building units of the polymeric chain may be linkages capable of bridging the units together for either in vitro or in vivo. For example the linkage may be a phosphorous containing linkage, e.g., phosphodiester or phosphothioate, or may be a nitrogen containing linkage, e.g., amide. It should further be understood that the chimeric polymer may contain non-nucleotide spacer molecules along with its other nucleotide or analogue units. Examples of spacer molecules which may be used are described in Nielsen et al. *Science*, 254:1497–1500 (1991).

Jennings et al., WO 94/13688 while discussing hammerhead ribozymes lacking the usual stem II base-paired region state:

One or more ribonucleotides and/or deoxyribonucleotides of the group $(X)_m$, [stem II] may be replaced, for example, with a linker selected from optionally substituted polyphosphodiester (such as poly(1-phospho-3-propanol)), optionally substituted alkyl, optionally substituted polyamide, optionally substituted glycol, and the like. Optional substituents are well known in the art, and include alkoxy (such as methoxy, ethoxy and propoxy), straight or branch chain lower alkyl such as $C_1$–$C_5$ alkyl), amine, aminoalkyl (such as amino $C_1$–$C_5$ alkyl), halogen (such as F, Cl and Br) and the like. The nature of optional substituents is not of importance, as long as the resultant endonuclease is capable of substrate cleavage.

Additionally, suitable linkers may comprise polycyclic molecules, such as those containing phenyl or cyclohexyl rings. The linker (L) may be a polyether such as polyphosphopropanediol, polyethyleneglycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenathrylene, aceanthrylene, triphenylene, pyrene, chrysene, naphthacene, thianthrene, isobenzofuran, chromene, xanthene, phenoxathiin, indolizine, isoindole, 3-H-indole, indole, 1-H-indazole, 4-H-quinolizine, isoquinoline, quinoline, phthalazine, naphthyridine, quinoxaline, quinazoline, cinnoline, pteridine, 4-αH-carbzole, carbazole, B-carboline, phenanthridine, acridine, perimidine, phenanthroline, phenazine, phenolthiazine, phenoxazine, which polycyclic compound may be substituted or modified, or a combination of the polyethers and the polycyclic molecules.

The polycyclic molecule may be substituted of polysubstituted with $C_1$–$C_5$ alkyl, alkenyl, hydroxyalkyl, halogen of haloalkyl group or with O—A or $CH_2$—O—A wherein A is H or has the formula CONR'R" wherein R' and R" are the same or different and are hydrogen or a substituted or unsubstituted $C_1$–$C_6$ alkyl, aryl, cycloalkyl, or heterocyclic group; or A has the formula —M—NR'R" wherein R' and R" are the same or different and are hydrogen, or a $C_1$–$C_5$ alkyl, alkenyl, hydroxyalkyl, or haloalkyl group wherein the halo atom is fluorine, chlorine, bromine, or iodine atom; and —M— is an organic moiety having 1 to 10 carbon atoms and is a branched or straight chain alkyl, aryl, or cycloalkyl group.

In one embodiment, the linker is tetraphosphopropanediol or pentaphosphopropanediol. In the case of polycyclic molecules there will be preferably 18 or more atoms bridging the nucleic acids. More preferably their will be from 30 to 50 atoms bridging, see for Example 5. In another embodiment the linker is a bifunctional carbazole or bifunctional carbazole linked to one or more polyphosphoropropanediol.

Such compounds may also comprise suitable functional groups to allow coupling through reactive groups on nucleotides."

SUMMARY OF THE INVENTION

This invention concerns the use of non-nucleotide molecules as spacer elements at the base of double-stranded nucleic acid (e.g., RNA or DNA) stems (duplex stems) or more preferably, in the single-stranded regions, catalytic core, loops, or recognition arms of enzymatic nucleic acids. Duplex stems are ubiquitous structural elements in enzymatic RNA molecules. To facilitate the synthesis of such stems, which are usually connected via single-stranded nucleotide chains, a base or base-pair mimetic may be used to reduce the nucleotide requirement in the synthesis of such molecules, and to confer nuclease resistance (since they are non-nucleic acid components). This also applies to both the catalytic core and recognition arms of a ribozyme. In particular abasic nucleotides (i.e., moieties lacking a nucleotide base, but having the sugar and phosphate portions) can be used to provide stability within a core of a ribozyme, e.g., at U4 or N7 or a hammerhead structure shown in FIG. 1.

Thus, in a first aspect, the invention features an enzymatic nucleic acid molecule having one or more non-nucleotide moieties, and having enzymatic activity to cleave an RNA or DNA molecule.

Examples of such non-nucleotide mimetics are shown in FIG. 6 and their incorporation into hammerhead ribozymes is shown in FIG. 7. These non-nucleotide linkers may be either polyether, polyamine, polyamide, or polyhydrocarbon compounds. Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jäschke et al., *Tetrahedron Lett.* 1993, 34:301; Ono et al., *Biochemistry* 1991, 30:9914; Arnold et al., International Publication No. WO 89/02439 entitled "Non-nucleotide Linking Reagents for Nucleotide Probes"; and Ferentz and Verdine, *J. Am. Chem. Soc.* 1991, 113:4000, all hereby incorporated by reference herein.

In preferred embodiments, the enzymatic nucleic acid includes one or more stretches of RNA, which provide the enzymatic activity of the molecule, linked to the non-nucleotide moiety.

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenine, guanine, cytosine, uracil or thymine. It may have substitutions for a 2' or 3' H or OH as described in the art. See Eckstein et al. and Usman et al., supra.

In preferred embodiments, the enzymatic nucleic acid includes one or more stretches of RNA, which provide the enzymatic activity of the molecule, linked to the non-nucleotide moiety. The necessary ribonucleotide components are known in the art, see, e.g., Usman, supra and Usman et al., *Nucl. Acid. Symp. Genes* 31:163, 1994.

As the term is used in this application, non-nucleotide-containing enzymatic nucleic acid means a nucleic acid molecule that contains at least one non-nucleotide component which replaces a portion of a ribozyme, e.g., but not limited to, a double-stranded stem, a single-stranded "catalytic core" sequence, a single-stranded loop or a single-stranded recognition sequence. These molecules are able to cleave (preferably, repeatedly cleave) separate RNA or DNA molecules in a nucleotide base sequence specific manner. Such molecules can also act to cleave intramolecularly if that is desired. Such enzymatic molecules can be targeted to virtually any RNA transcript. Such molecules also include nucleic acid molecules having a 3' or 5' non-nucleotide, useful as a capping group to prevent exonuclease digestion.

Enzymatic molecules of this invention act by first binding to a target RNA or DNA. Such binding occurs through the target binding portion of the enzyme which is held in close proximity to an enzymatic portion of molecule that acts to cleave the target RNA or DNA. Thus, the molecule first recognizes and then binds a target nucleic acid through complementary base-pairing, and once bound to the correct site, acts enzymatically to cut the target. Strategic cleavage of such a target will destroy its ability to direct synthesis of an encoded protein. After an enzyme of this invention has bound and cleaved its target it is released from that target to search for another target, and can repeatedly bind and cleave new targets.

The enzymatic nature of an enzyme of this invention is advantageous over other technologies, such as antisense technology (where a nucleic acid molecule simply binds to a nucleic acid target to block its translation) since the effective concentration of the enzyme necessary to effect a therapeutic treatment is lower than that of an antisense oligonucleotide. This advantage reflects the ability of the enzyme to act enzymatically. Thus, a single enzyme molecule is able to cleave many molecules of target RNA. In addition, the enzyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the target and so specificity is defined as the ratio of the rate of cleavage of the targeted nucleic acid over the rate of cleavage of non-targeted nucleic acid. This cleavage mechanism is dependent upon factors additional to those involved in base pairing. Thus, it is thought that the specificity of action of an enzyme of this invention is greater than that of antisense oligonucleotide binding the same target site.

By "complementarity" is meant a nucleic acid that can form hydrogen bond(s) with other RNA sequence by either traditional Watson-Crick or other non-traditional types (for example, Hoogsteen type) of base-paired interactions.

By the phrase enzyme is meant a catalytic non-nucleotide-containing nucleic acid molecule that has complementarity in a substrate-binding region to a specified nucleic acid target, and also has an enzymatic activity that specifically cleaves RNA or DNA in that target. That is, the enzyme is able to intramolecularly or intermolecularly cleave RNA or DNA and thereby inactivate a target RNA or DNA molecule. This complementarity functions to allow sufficient hybridization of the enzymatic molecule to the target RNA or DNA to allow the cleavage to occur. One hundred percent complementarity is preferred, but complementarity as low as 50–75% may also be useful in this invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistry* 28, 4929, and Hampel at al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 Biochemistry 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the nucleic acid of a desired target. The enzyme molecule is preferably targeted to a highly conserved sequence region of a target such that specific treatment of a disease or condition can be provided with a single enzyme. Such enzyme molecules can be delivered exogenously to specific cells as required. In the preferred hammerhead motif the small size (less than 60 nucleotides, preferably between 30–40 nucleotides in length) of the molecule allows the cost of treatment to be reduced compared to other ribozyme motifs.

Synthesis of nucleic acids greater than 100 nucleotides in length is difficult using automated methods, and the therapeutic cost of such molecules is prohibitive. In this invention, small enzyme motifs (e.g., of the hammerhead structure) are used for exogenous delivery. The simple structure of these molecules increases the ability of the enzyme to invade targeted regions of mRNA structure. Unlike the situation when the hammerhead structure is included within longer transcripts, there are no non-enzyme flanking sequences to interfere with correct folding of the enzyme structure or with complementary regions.

Other features and advantages of the invention will be apparent from the following description of the preferred embodiments thereof, and from the claims.

DESCRIPTION OF THE PREFERRED EMBODIMENTS

The drawings will first briefly be described.

Drawings:

FIG. 1 is a diagrammatic representation of a hammerhead ribozyme domain known in the art. Stem II can be $\geq 2$ base-pair long, or can even lack base pairs and consist of a loop region.

FIG. 2*a* is a diagrammatic representation of the hammerhead ribozyme domain known in the art; FIG. 2*b* is a diagrammatic representation of the hammerhead ribozyme as divided by Uhlenbeck (1987, *Nature*, 327, 596) into a substrate and enzyme portion; FIG. 2*c* is a similar diagram showing the hammerhead divided by Haseloff and Gerlach (1988, *Nature*, 334, 585) into two portions; and FIG. 2*d* is a similar diagram showing the hammerhead divided by Jeffries and Symons (1989, *Nucleic. Acids. Res.*, 17, 1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H , refers to bases A, U or C. Y refers to pyrimidine bases. "___" refers to a chemical bond.

FIG. 4 is a representation of the general structure of the hepatitis delta virus ribozyme domain known in the art (Perrota and Been, 1991 supra).

FIG. 5A is a representation of the general structure of the self-cleaving Neurospora VS RNA domain. FIG. 5B is a line diagram representing the "I" ribozyme motif. The figure shows the "Upper" and the "Lower" base-paired regions linked by the "connecting" region. IV (left) and V (right) shows the left and the right handed regions within the "upper" region, respectively. II (left) and VI (right) shows the left and the right handed regions within the "lower" region, respectively).

FIGS. 6A and 6B are diagrammatic representations of various non-nucleotide mimetics that may be incorporated into nucleic acid enzymes. Standard abbreviations are used in the Figure. In compound 1 each X may independently be oxygen, nitrogen, sulfur or substituted carbons containing alkyl, alkene or equivalent chains of length 1–10 carbon atoms. In compounds 6, 6a, 7, 8, 9 and 10 each Y may independently be a phosphodiester, ether or amide linkage to the rest of the nucleic acid enzyme. In compounds 4 and 5 each R may independently be H, OH, protected OH, O-alkyl, alkenyl or alkynyl or alkyl, alkenyl or alkynyl of 1–10 carbon atoms.

FIG. 7 is a diagrammatic representation of the preferred location for incorporation of various non-nucleotide mimetics into nucleic acid enzymes. Specifically, mimetics, 1–10, may replace the loop (denoted as L/in FIG. 7) that connects the two strands of Stem II. Stem II itself may be from 1 to 10 base pairs. In examples 1 & 2 below compounds 1 and 2 were incorporated into molecules having a stem II of 1 to 5 basepairs in length. Compounds 1, 4 and 5 may also replace nucleotides in the recognition arms of stems I and III or in stem II itself.

Figure 10A:
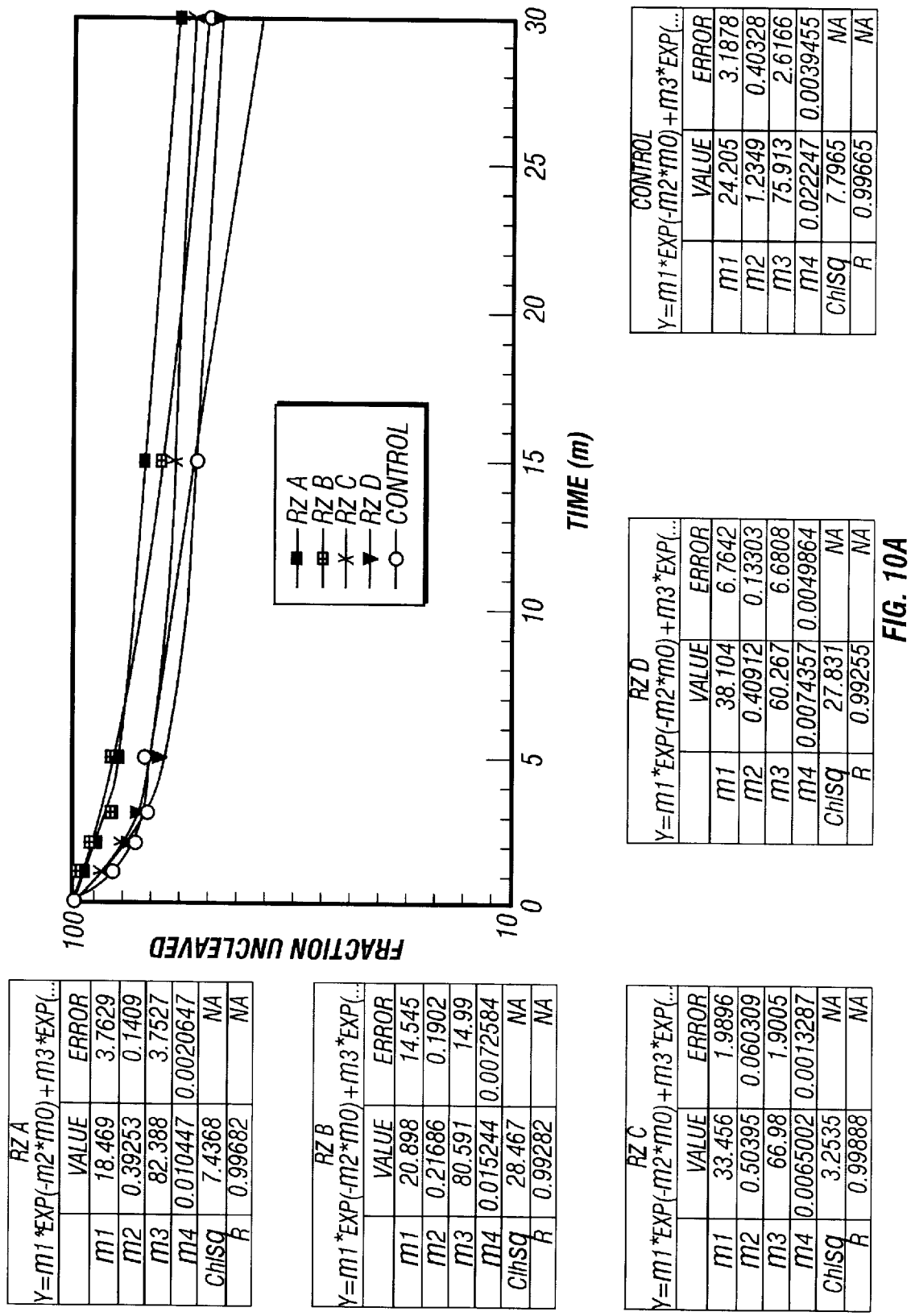
Figure 10B:
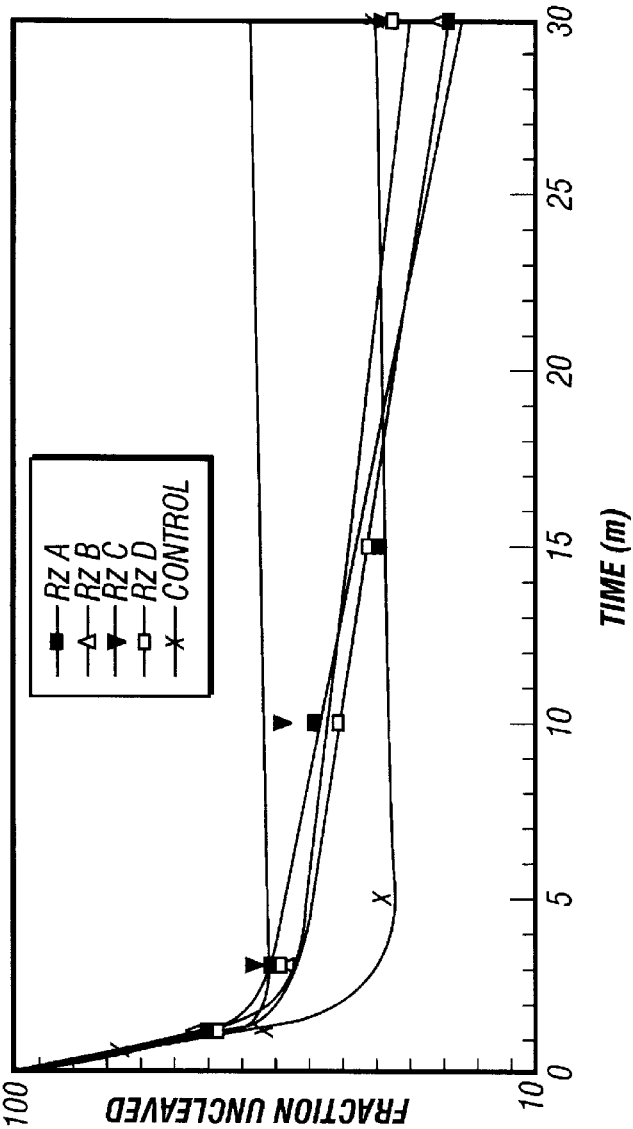

FIGS. 10*a* and 10*b* are graphical representations of cleavage of substrate by various ribozymes at 8 nM, or 40 nM, respectively.

Figure 11:
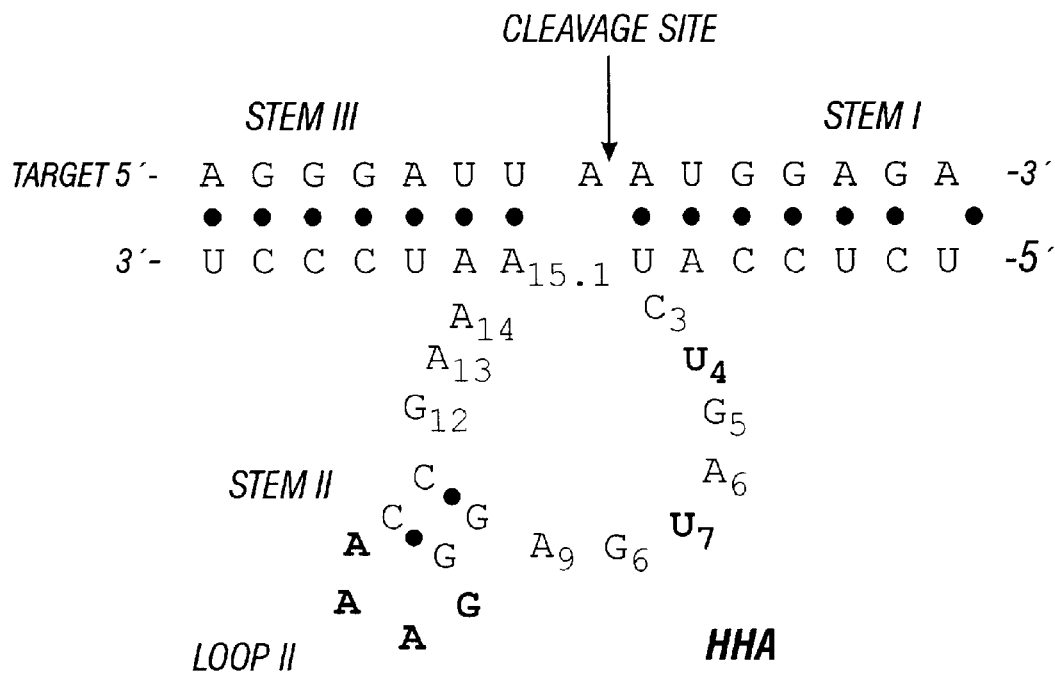

FIG. 11 is a diagrammatic representation of a hammerhead ribozyme targeted to site A (HHA). Arrow indicates the cleavage site. Stem II is shorter than usual for a hammerhead ribozyme.

Figure 12:
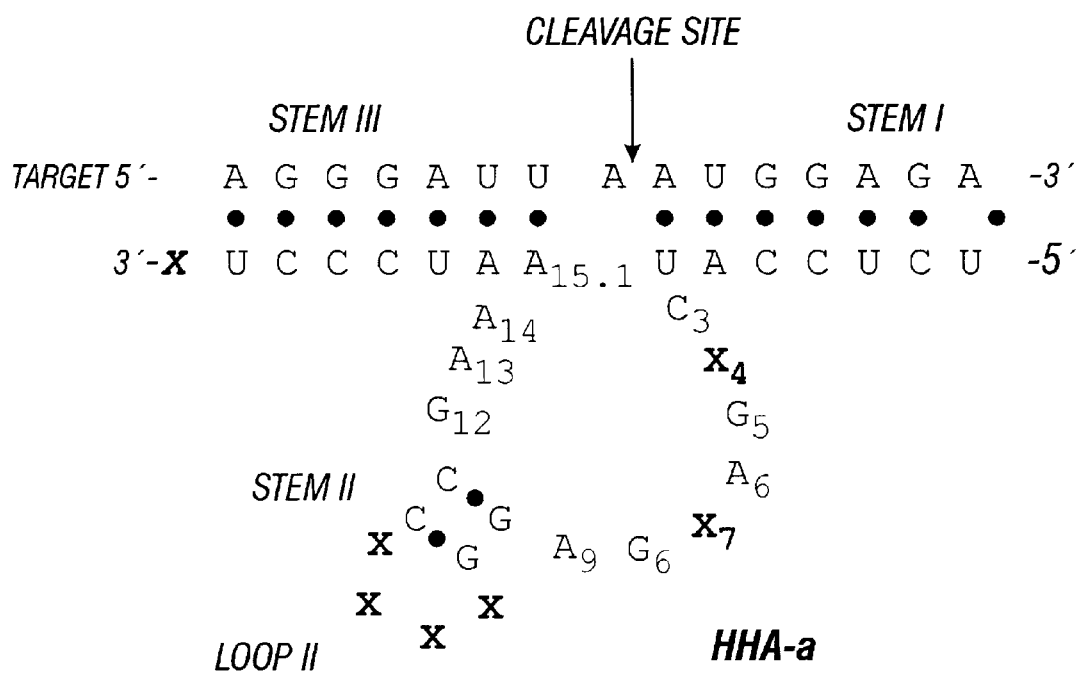

FIG. 12 is a diagrammatic representation of HHA ribozyme containing abasic substitutions (HHA-a) at various positions. Ribozymes were synthesized as described in the application. "X" shows the positions of abasic substitutions. The abasic substitutions were either made individually or in certain combinations.

Figure 13:
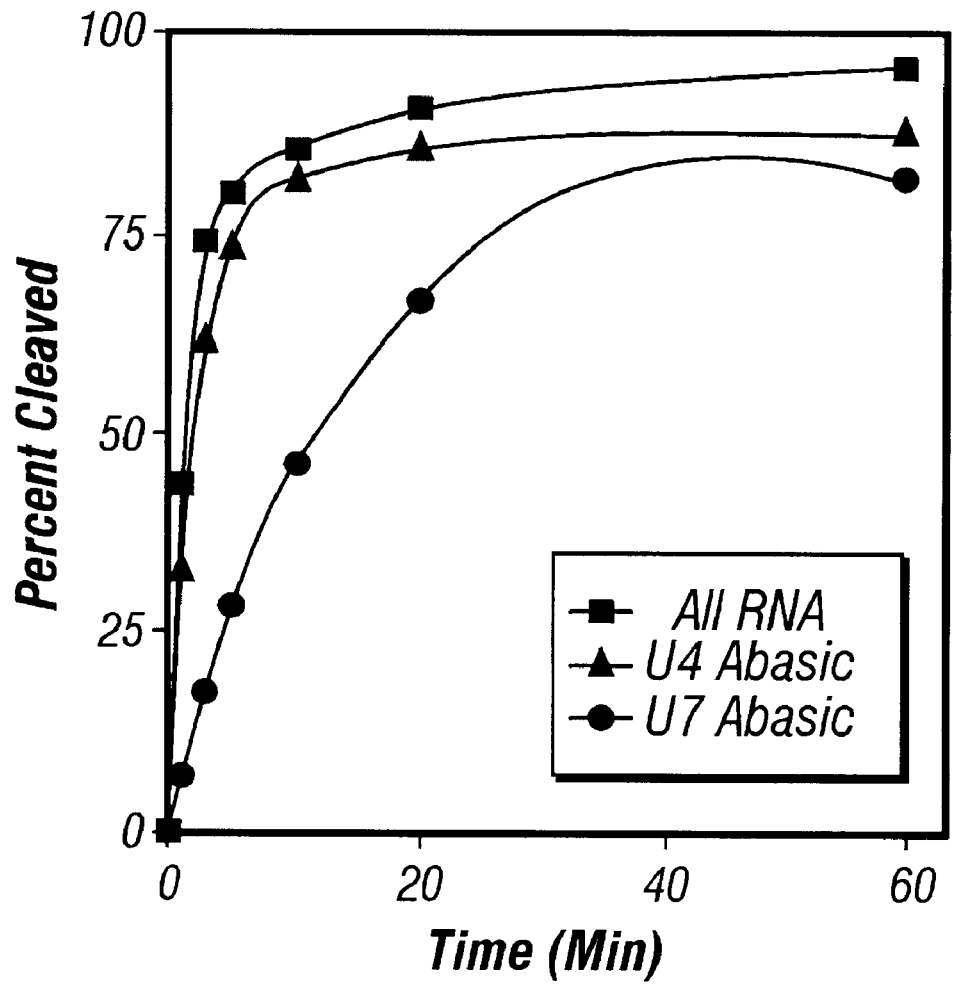

FIG. 13 shows the in vitro RNA cleavage activity of HHA and HHA-a ribozymes. All RNA, refers to HHA ribozyme containing no abasic substitution. U4 Abasic, refers to HHA-a ribozyme with a single abasic (ribose) substitution at position 4. U7 Abasic, refers to HHA-a ribozyme with a single abasic (ribose) substitution at position 7.

Figure 14:
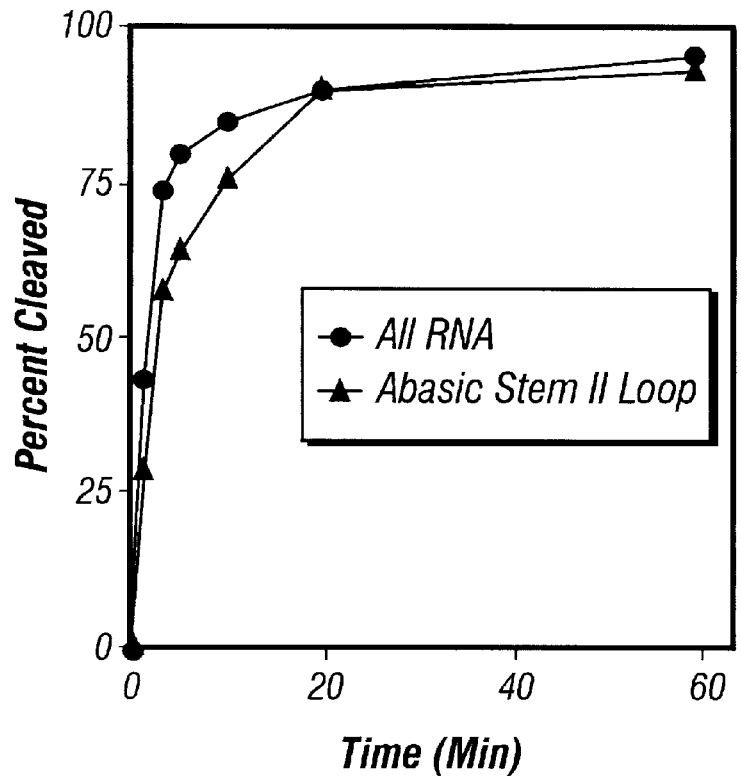

FIG. 14 shows in vitro RNA cleavage activity of HHA and HHA-a ribozymes. Abasic Stem II Loop, refers to HHA-a ribozyme with four abasic (ribose) substitutions within the loop in stem II.

Figure 15:
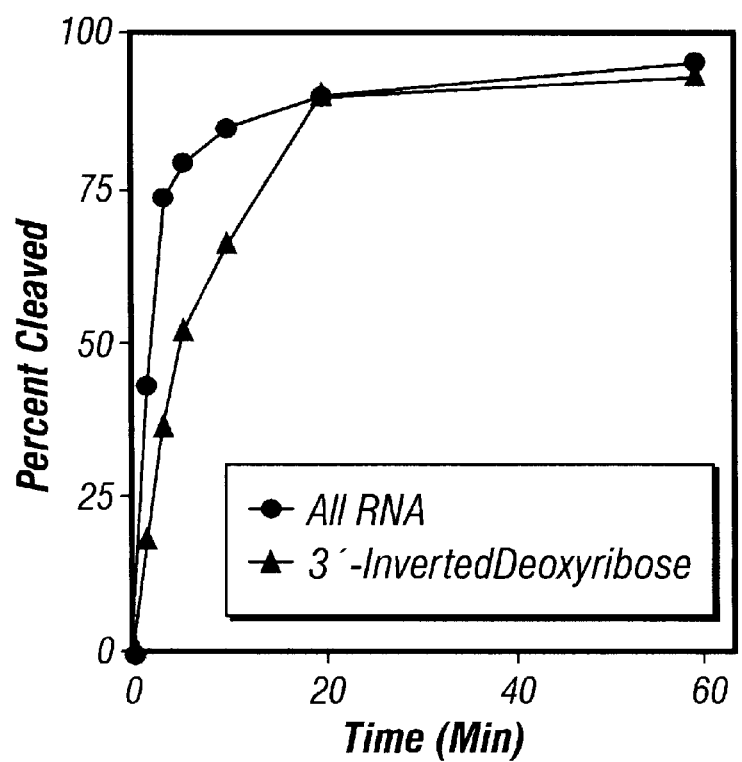

FIG. 15 shows in vitro RNA cleavage activity of HHA and HHA-a ribozymes. 3'-lnverted Deoxyribose, refers to HHA-a ribozyme with an inverted deoxyribose (abasic) substitution at its 3' termini.

Figure 16:
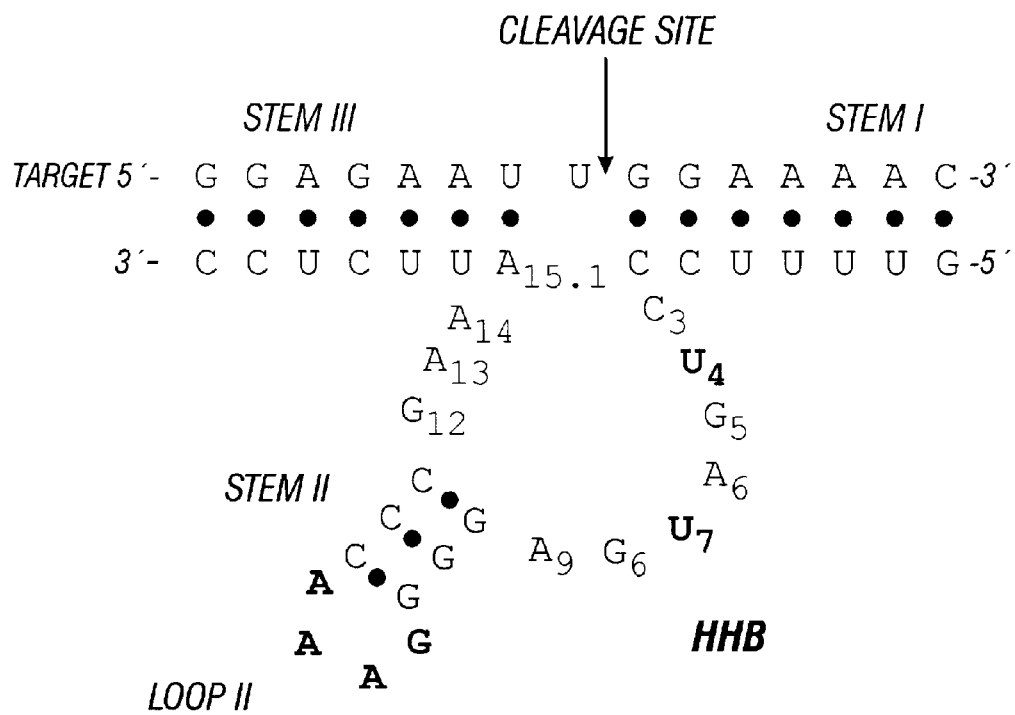

FIG. 16 is a diagrammatic representation of a hammerhead ribozyme targeted to site B (HHB). Target B is involved in the proliferation of mammalian smooth muscle cells. Arrow indicates the site of cleavage. Inactive version of HHB contains 2 base-substitutions (G5U and A15.1U) that renders the ribozyme catalytically inactive.

Figure 17:
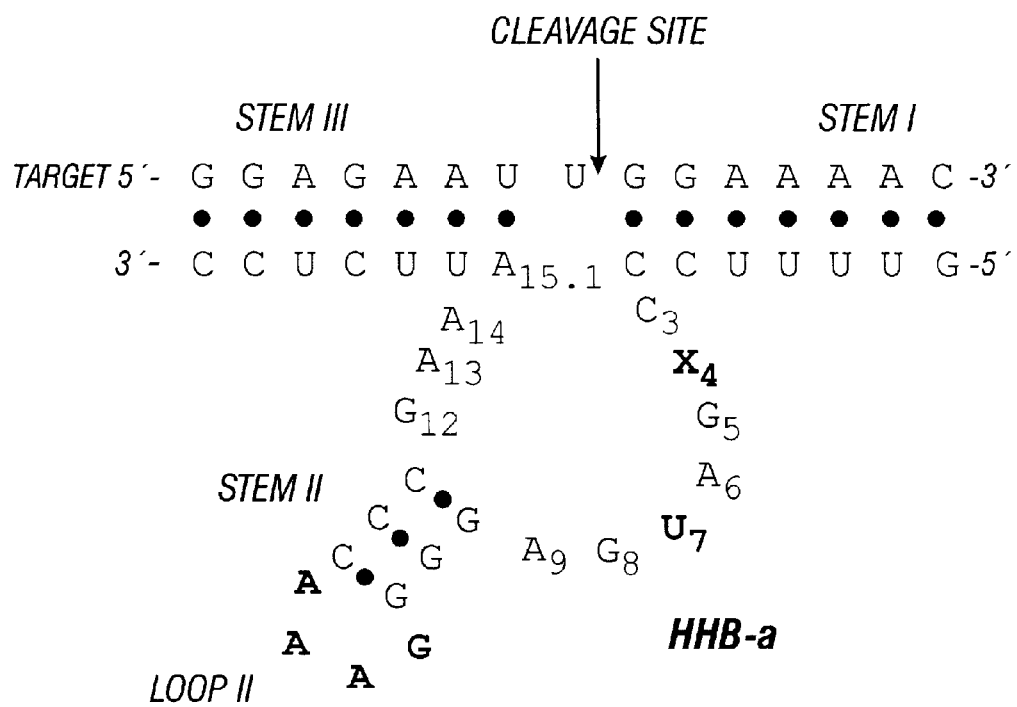

FIG. 17 is a diagrammatic representation of HHB ribozyme with abasic substitution (HHB-a) at position 4. X, shows the position of abasic substitution.

Figure 18:
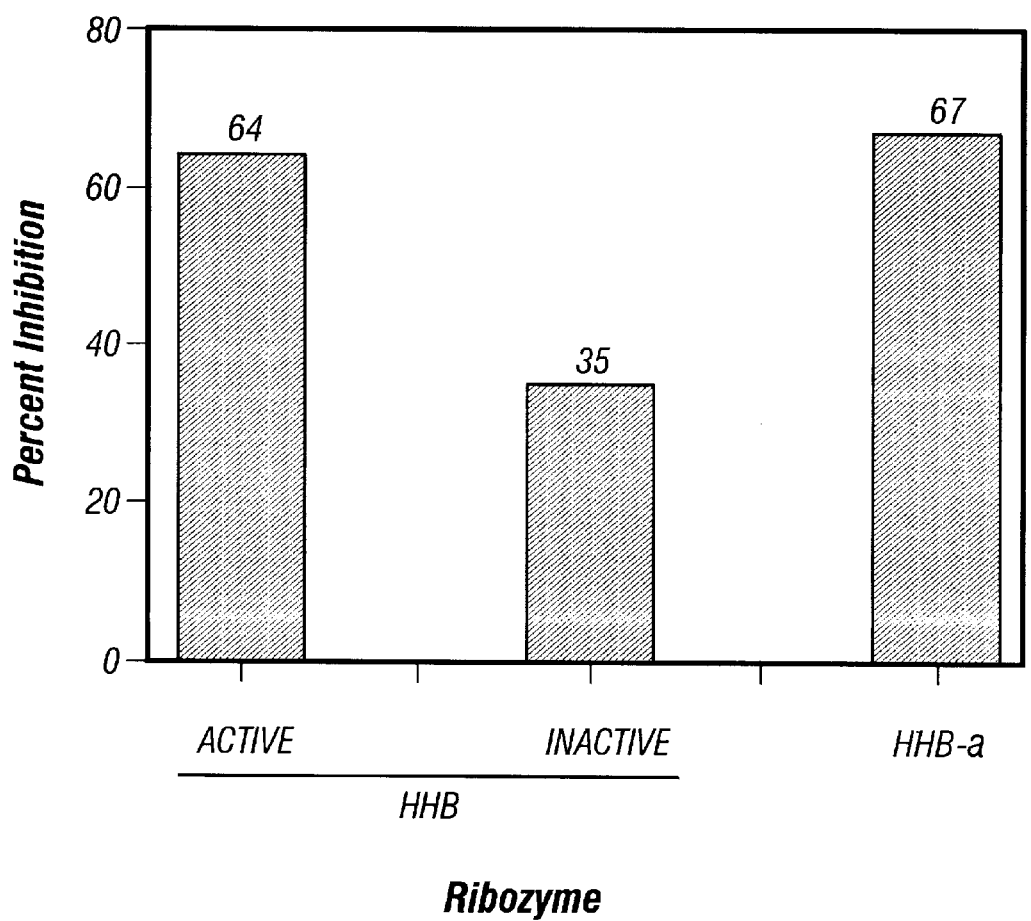

FIG. 18 shows ribozyme-mediated inhibition of rat aortic smooth muscle cell (RASMC) proliferation. Both HHB and HHB-a ribozymes can inhibit the proliferation of RASMC in culture. Catalytically inactive HHB ribozyme shows inhibition which is significantly lower than active HHB and HHB-a ribozymes.

NON-NUCLEOTIDE MIMETICS

Non-nucleotide mimetics useful in this invention are generally described above. Those in the art will recognize that these mimetics can be incorporated into an enzymatic molecule by standard techniques at any desired location. Suitable choices can be made by standard experiments to determine the best location, e.g., by synthesis of the molecule and testing of its enzymatic activity. The optimum molecule will contain the known ribonucleotides needed for enzymatic activity, and will have non-nucleotides which change the structure of the molecule in the least way possible. What is desired is that several nucleotides can be substituted by one non-nucleotide to save synthetic steps in enzymatic molecule synthesis and to provide enhanced stability of the molecule compared to RNA or even DNA.
Synthesis of Ribozymes In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. The ribozymes are chemically synthesized. The method of synthesis used follows the procedure for normal RNA synthesis as described in Usman et al., 1987 *J. Am. Chem. Soc.*, 109, 7845 and in Scaringe et al., 1990 *Nucleic Acids Res.*, 18, 5433 and makes use of common nucleic acid protecting and coupling groups, such as dimethoxytrityl at the 5'-end, and phosphoramidites at the 3'-end. The average stepwise coupling yields were >98%.

Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

Figure 1:
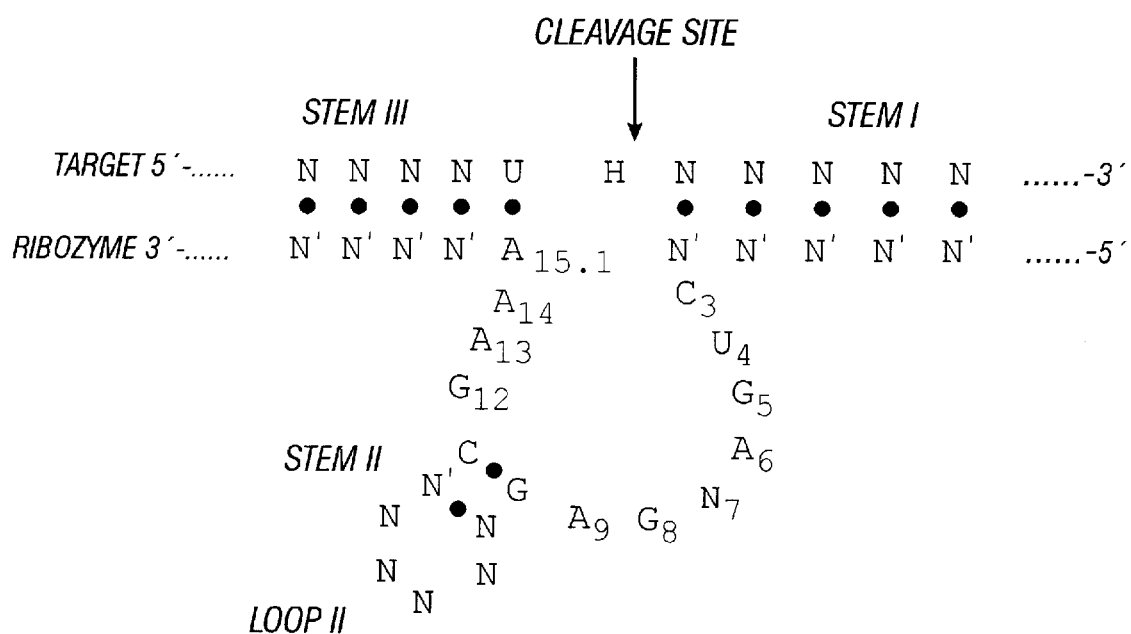
Figure 2A:
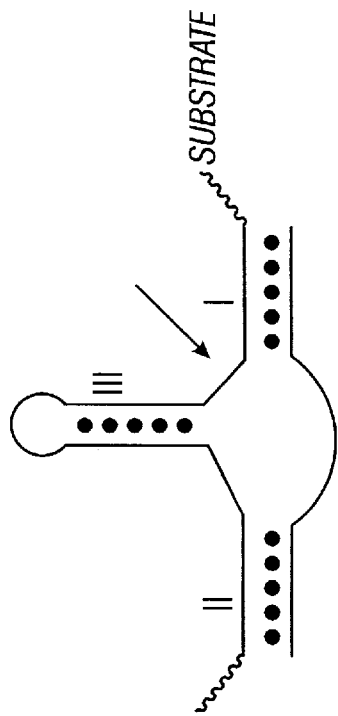
Figure 2B:
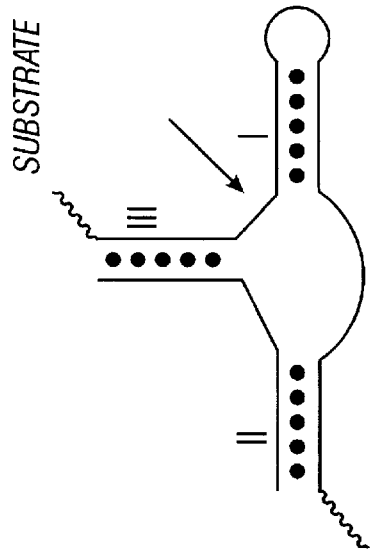
Figure 2C:
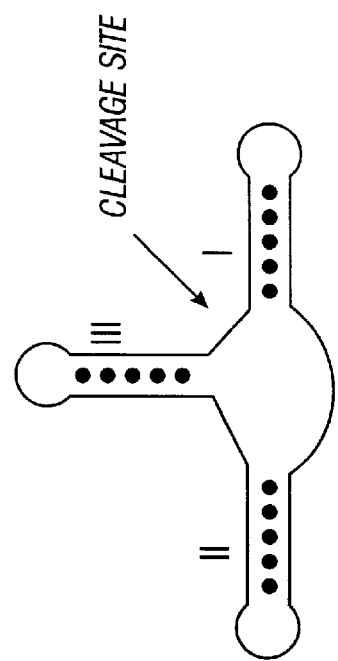
Figure 2D:
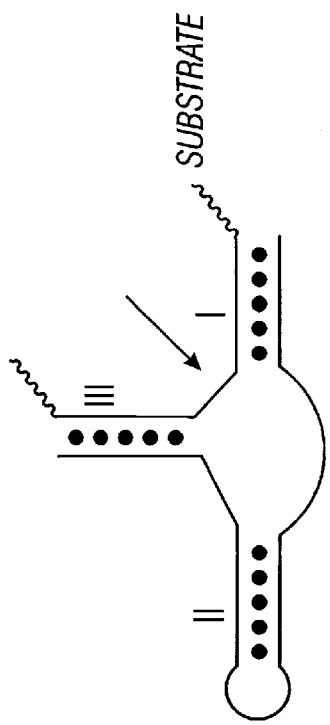
Figure 3:
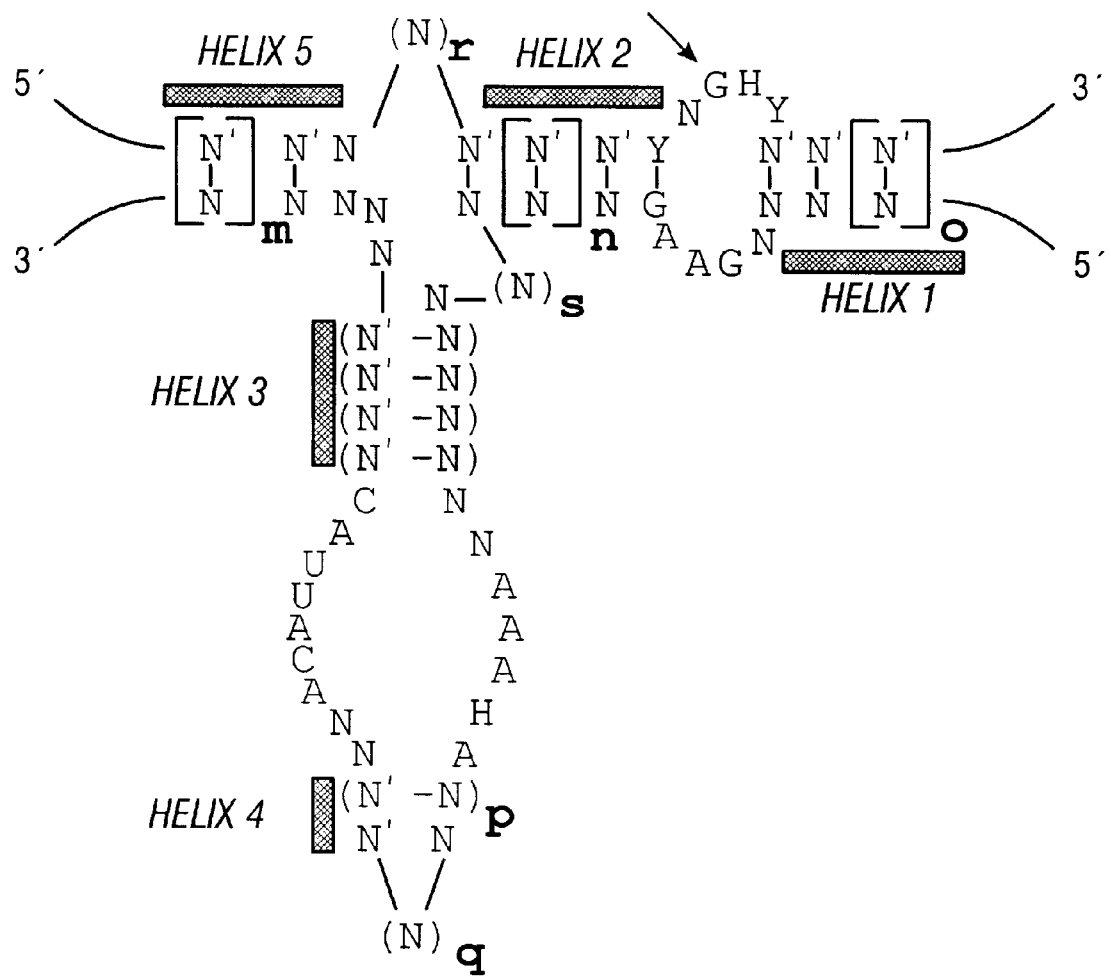
Figure 4:
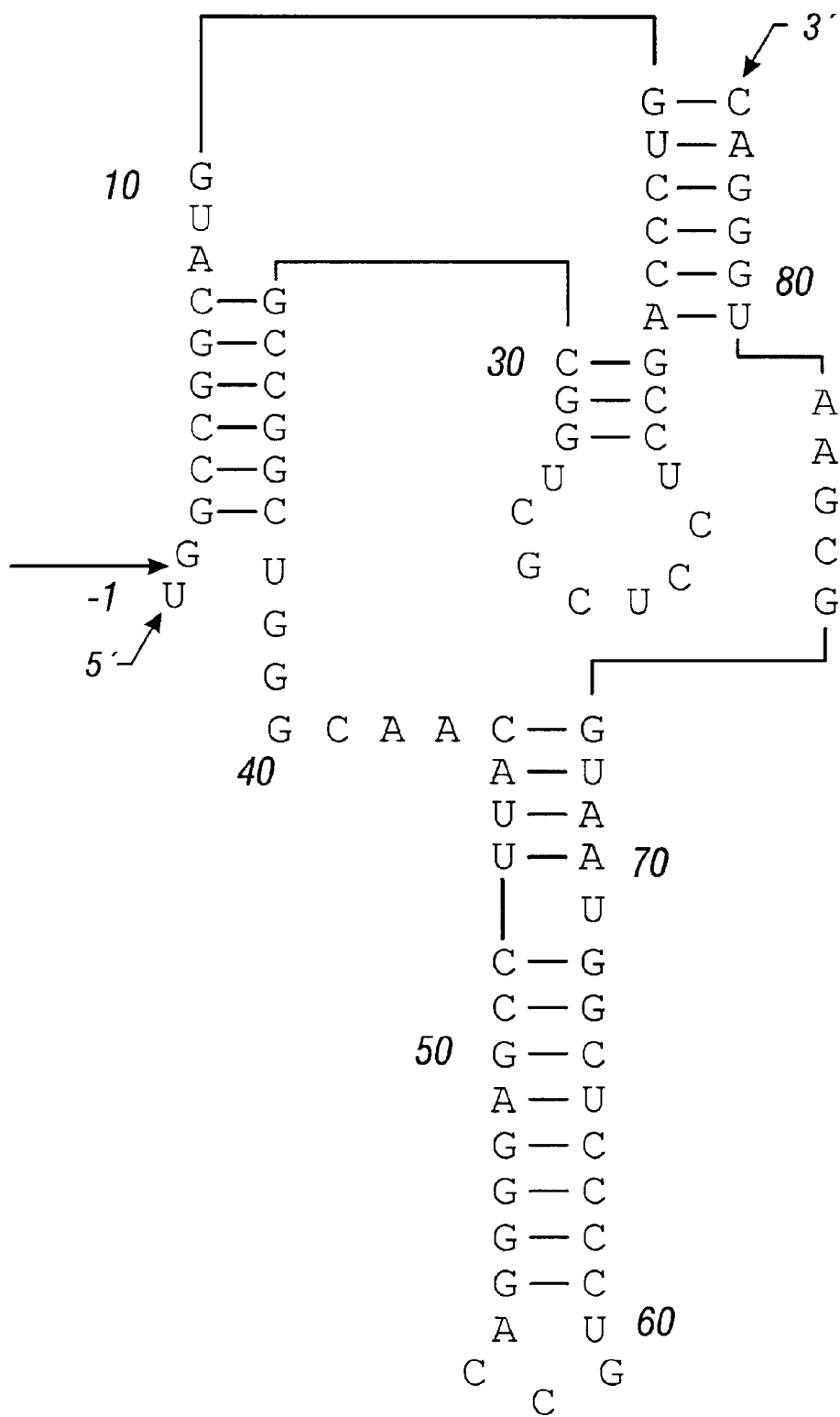
Figure 5A:
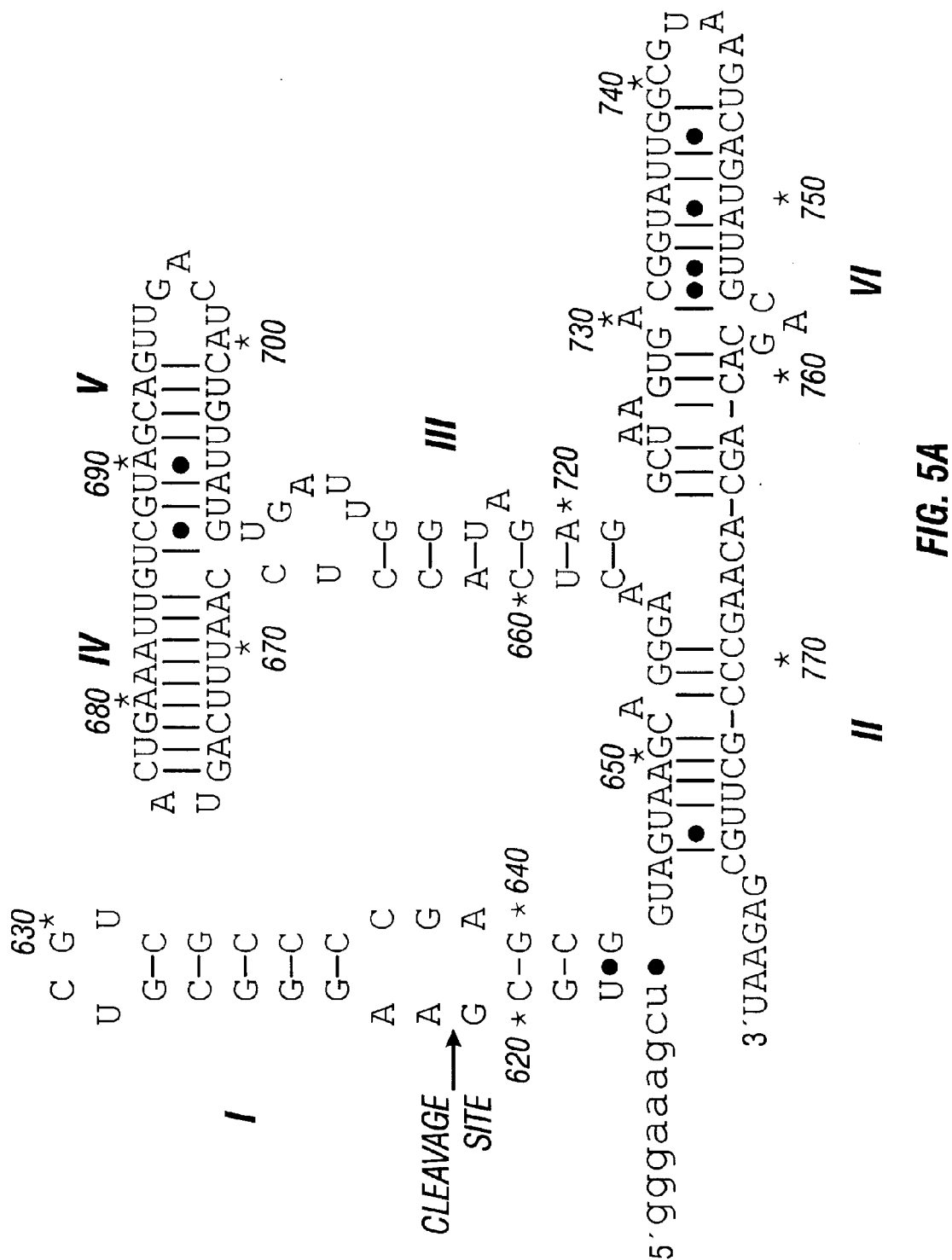
Figure 5B:
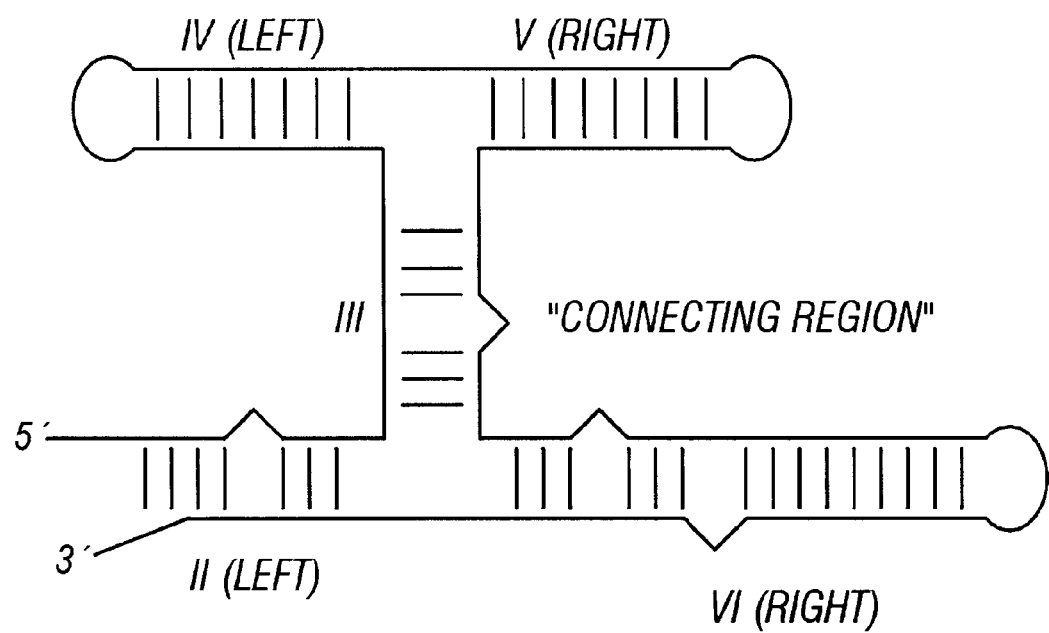

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.
Optimizing Ribozyme Activity Ribozyme activity can be optimized as described by Stinchcomb et al., "Method and Composition for Treatment of Restenosis and Cancer Using Ribozymes," filed May 18, 1994, U.S. Ser. No. 08/245,466. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application Ser. No. 07/829,729, and Sproat, European Patent Application 92110298.4 which describe various chemical modifications that can be made to the sugar moieties of enzymatic RNA molecules. Modifications which enhance their efficacy in cells, and removal of stem II bases to shorten RNA synthesis times and reduce chemical requirements (All these publications are hereby incorporated by reference herein).
Administration of Ribozyme Sullivan et al., PCT WO94/02595, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al, PCT WO93/23569 which have been incorporated by reference herein.

EXAMPLES

The following are non-limiting examples showing the synthesis of non-nucleotide mimetic-containing catalytic nucleic acids using non-nucleotide phosphoramidites.

Figure 7:
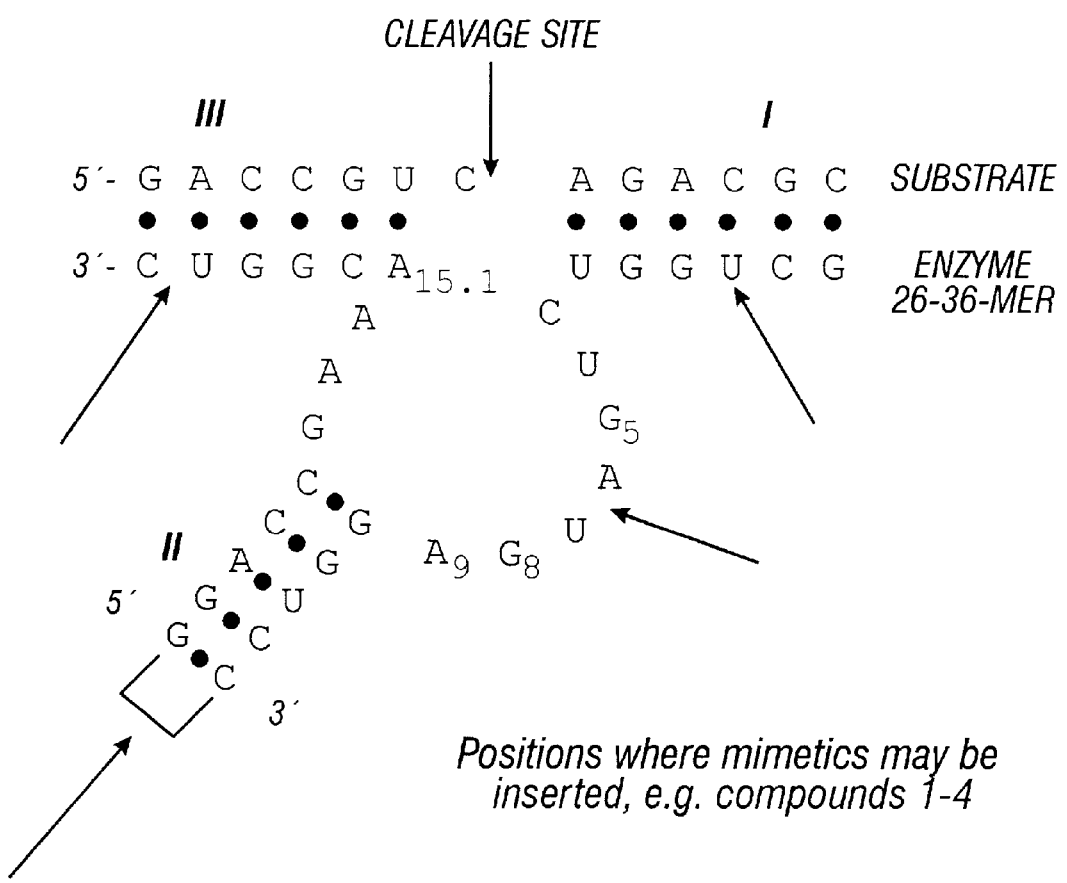
Figure 8:
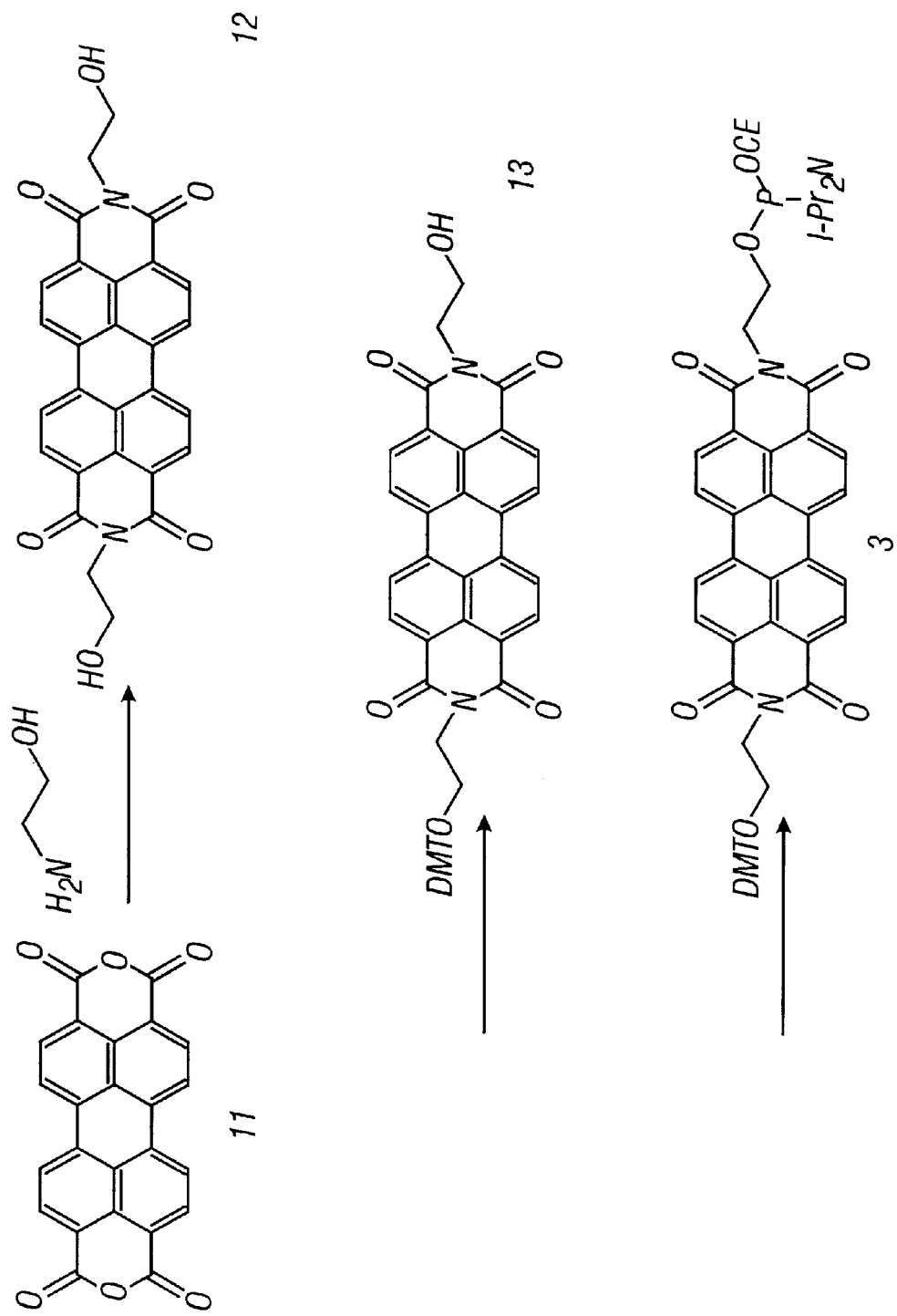
FIG. 8 is a diagrammatic representation of the synthesis of a perylene based non-nucleotide mimetic phosphoramidite 3.

As shown in FIG. 7, such non-nucleotides can be located in the binding arms, core or the loop adjacent stem II of a hammerhead type ribozyme. Those in the art following the teachings herein can determine optimal locations in these regions. Surprisingly, abasic moieties can be located in the core of such a ribozyme.

Example 1

Figure 6A:
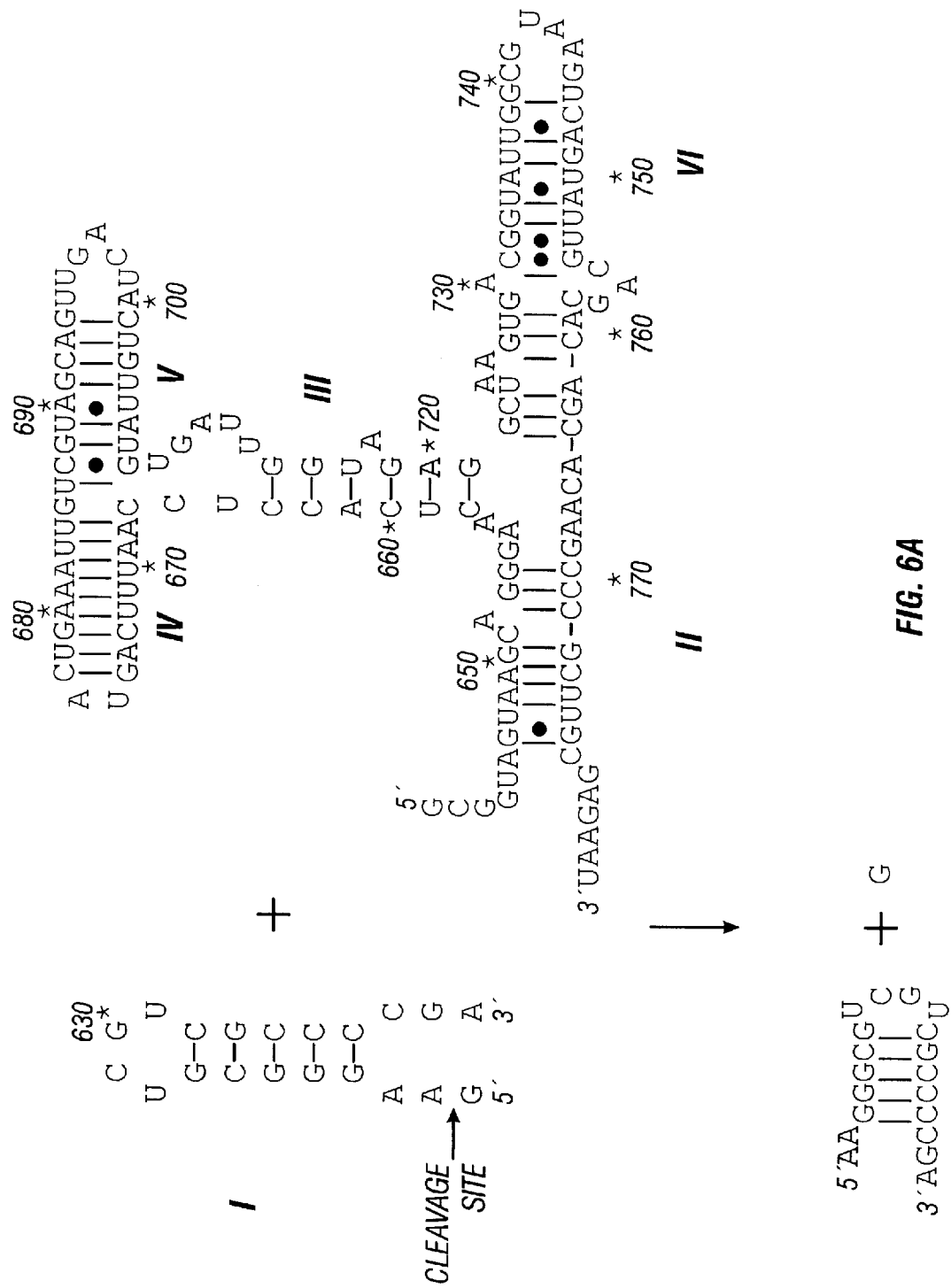
Figure 6B:
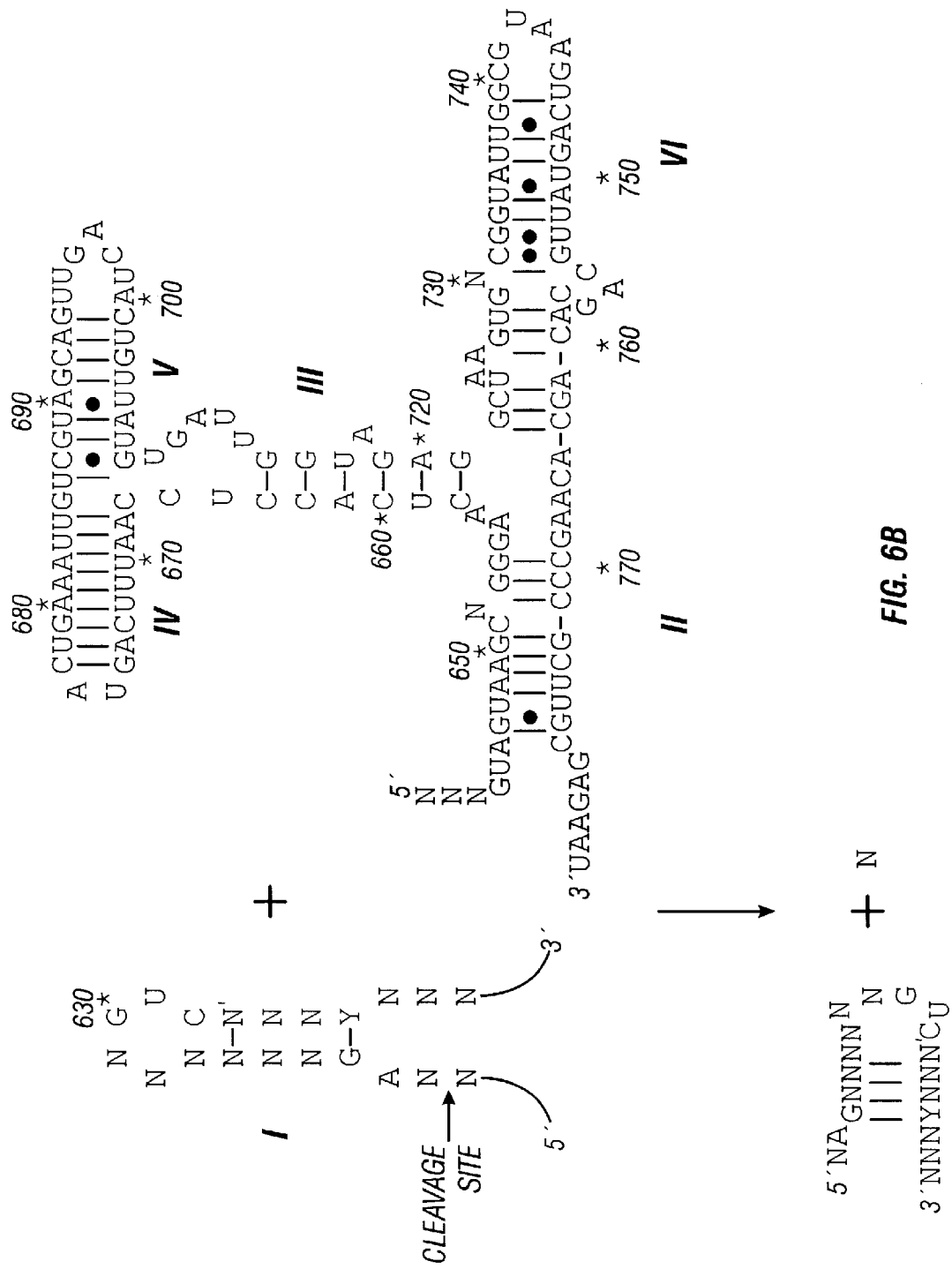

Synthesis of Hammerhead Ribozymes Containing Non-nucleotide Mimetics: Polyether Spacers Polyether spacers, compound 1 (FIG. 6; X=0, n=2 or 4), have been incorporated both singly, n=2 or 4, or doubly, n=2, at the base of stem II of a hammerhead ribozyme, replacing loop 2, and shown to produce a ribozyme which has lower catalytic efficiency. The method of synthesis used followed the procedure for normal RNA synthesis as described in Usman et al., *J. Am. Chem. Soc.* 1987, 109:7845 and in Scaringe et al., *Nucleic Acids Res.* 1990, 18:5433, and makes use of common nucleic acid protecting and coupling groups, such as dimethoxytrityl at the 5'-end, and phosphoramidites at the 3'-end. The average stepwise coupling yields were >98%. The design of these types of mimetics has not been optimized to date, but, as discussed above, this can be readily achieved using standard experimental techniques. These experiments indicate the potential of such mimetics to replace the loops and portions of stems in ribozymes while maintaining catalytic activity. These mimetics may be incorporated not only into hammerhead ribozymes, but also into hairpin, hepatitis delta virus, or Group 1 or Group 2 introns. They are, therefore, of general use as replacement motifs in any nucleic acid structure. Use of such mimetics allows about 2–10 nucleotides to be omitted from the final nucleic acid molecule compared to the use of an oligonucleotide without a non-nucleotide mimetic.

Example 2

Synthesis of Hammerhead Ribozymes Containing Non-nucleotide Mimetics: Aromatic Spacers In another example, a specific linker for the base of the stem II C-G of a hammerhead ribozyme was designed. Applicant believes that the distance between the C1' carbons of the C-G base pair is about 16 Angstroms. To join these two pieces of RNA by a covalent analog of the C-G base pair a new type of dimer phosphoramidite containing a linker between the 3'-OH and the 5'-OH of the G and C residues respectively can be constructed. Two types of base-pair mimetic are the rigid aromatic spacers, 2 or 3, shown in FIG. 6. These have been incorporated at the base of stem II of a hammerhead ribozyme as described in Example 1, replacing loop 2, and shown to produce a ribozyme which has lower catalytic efficiency. Another mimetic is a flexible alkyl spacer similar to the polyamide backbone described by Nielsen et al., *Science* 1991, 254:1497 (see, FIG. 6; 6 or a derivative thereof 6a; Zuckerman et al., *J. Am. Chem. Soc.* 1992, 114:10646). Use of such mimetics allows about 2–10 nucleotides to be omitted from the final nucleic acid molecule compared to the use of an oligonucleotide without a non-nucleotide mimetic.

Example 3

Synthesis of Non-nucleotide Mimetics Aromatic Spacer Phosphoramidite 2

This compound was originally described by Salunkhe et al., *J. Am. Chem. Soc.* 1992, 114:8768. The synthesis was modified as follows: To terphthalic acid (1.0 g, 6.0 mmol) in DMF (12 mL) was added EDC (2.54 g, 13.2 mmol), aminohexanol (1.55 g, 13.2 mmol) and N-methylmorpholine (1.45 mL, 13.2 mmol). The reaction mixture was stirred overnight at which time the solution was cloudy. Water was added to the reaction mixture to precipitate out the product. The solid was filtered and washed with water and dried to provide 562 mg (25.7%) of the diol.

To the diol (250 mg, 0.687 mmol) in DMSO (40 mL) was added triethylamine (287 µL, 2.06 mmol), dimethoxytrityl chloride (220 mg, 0.653 mmol) and catalytic DMAP. The reaction mixture was heated to 40° C. and stirred overnight. The mixture was then cooled to room temperature (about 20–25° C.), quenched with water and extracted three times with EtOAc. A solid precipitate remained in the organic layer that was isolated and found to be starting diol (50 mg, 20%). The organic layer was dried over $Na_2SO_4$ and evaporated. The resulting oil was purified with flash chromatography (10% EtOAc in hexanes to 100% EtOAc) to yield 250 mg (55%) of the monotritylated compound.

To the alcohol (193 mg, 0.29 mmol) in THF (1 mL) at 0° C. was added diisopropylethylamine (101 µL, 0.58 mmol) and then 2-cyanoethyl N,N-diisopropylamino chlorophosphoramidite (78 µL, 0.35 mmol) dropwise. The resulting mixture was stirred for 5 minutes and then warmed to room temperature. After 1 hour the reaction mixture was quenched with methanol and evaporated. The resulting oil was purified by flash chromatography (1:1 hexanes:EtOAc) to yield 158 mg (63%) of the phosphoramidite.

Example 4

Synthesis of Non-nucleotide Mimetics Aromatic Spacer Phosphoramidite 3

Referring to FIG. 8, to 3, 4, 9, 10-perylenetetracarboxylic dianhydride 11 (1.0 g, 2.55 mmol) in quinoline (10 mL) was added ethanolamine (919 µL, 15.3 mmol) and ZnOAc.2.5 $H_2O$ (140 mg, 0.638 mmol). The reaction mixture was heated to 190° C. for 8 hours. The solution was then cooled, 1N HCl added to precipitate the product and the mixture was filtered. The solid was washed with hot 10% $CaCO_3$ until the filtrate was no longer pale green. The remaining bright red precipitate 12 was then dried.

The resulting diol 12 was then treated as outlined above for 2 to provide the phosphoramidite 3.

Example 5

Synthesis of Hammerhead Ribozymes Containing Non-nucleotide Mimetics: Abasic Nucleotides 4 and 5

Figure 9A:
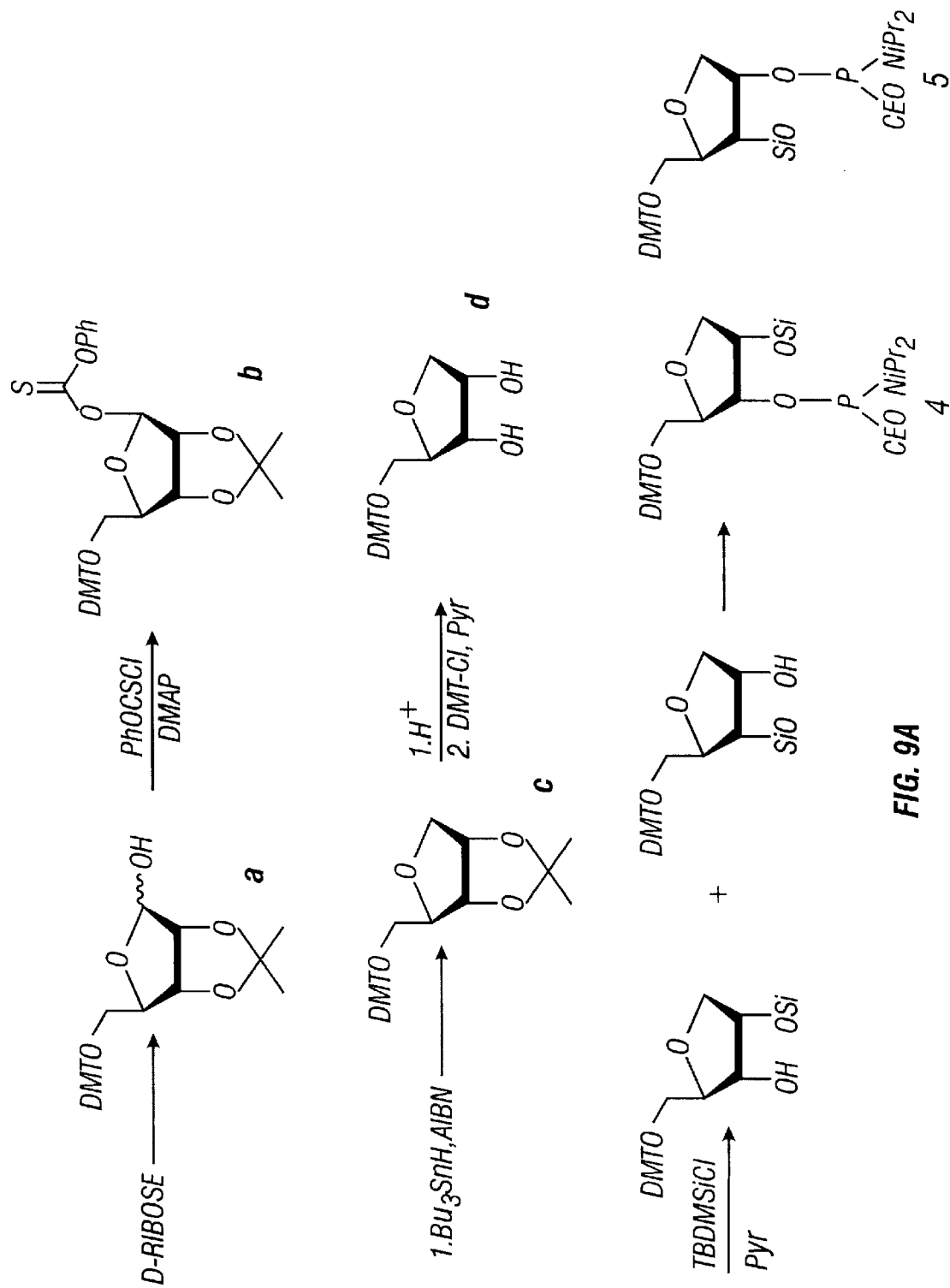
FIGS. 9A and 9B are diagrammatic representations of the synthesis of an abasic deoxyribose or ribose non-nucleotide mimetic phosphoramidite.

Compound 4, R=H, was prepared according to Iyer et al., *Nucleic Acids Res.* 1990, 18:2855. Referring to FIG. 9A, compounds 4 and 5 (R=O-t-butyidimethylsilyl) phosphoramidites were prepared as follows:

To a solution of D-ribose (20.0 g, 0.105 mol) in N,N-dimethylformamide (250 mL) was added 2,2-dimethoxypropane (50 mL) and p-toluenesulfonic acid monohydrate (300 mg). The reaction mixture was stirred for 16 hours at room temperature and then evaporated to dryness. The crude product was coevaporated with pyridine (2×150 mL), dissolved in dry pyridine (300 mL) and 4,4'-dimethoxytrityl chloride (37.2 g, 0.110 mol) was added and stirred for 24 hours at room temperature. The reaction mixture was diluted with methanol (50 mL) and evaporated to dryness. The residue was dissolved in chloroform (800 mL) and washed with 5% $NaHCO_3$ (2×200 mL), brine (300 mL), dried, evaporated, coevaporated with toluene (2×100 mL) and purified by flash chromatography in CHCl$_3$ to yield 40.7 g (78.1%) of compound a.

To a solution of dimethoxytrityl derivative a (9.0 g, 18.3 mmol) and DMAP (4.34 g, 36 mmol) in dry CH$_3$CN, phenoxythiocarbonyl chloride (3.47 g, 20.1 mmol) was added dropwise under argon. The reaction mixture was left for 16 hours at room temperature, then evaporated to dryness. The resulting residue was dissolved in chloroform (200 mL), washed with 5% NaHCO$_3$, brine, dried, evaporated and purified by flash chromatography in CHCl$_3$, to yield 8.0 g (69.5%) of compound b as the β-anomer.

To a solution of intermediate b (3.0 g, 4.77 mmol) in toluene (50 mL) was added AIBN (0.82 g, 5.0 mmol) and Bu$_3$SnH (1.74 g, 6.0 mmol) under argon and the reaction mixture was kept at 80° C. for 7 hours. The solution was evaporated and the resulting residue purified by flash chromatography in CHCl$_3$ to yield 1.5 g (66%) of protected ribitol C.

Subsequent removal of all protecting groups by acid treatment and tritylation provided the protected ribitol d which was then converted to target phosphoramidites 4 and 5 by the general method described in Scaringe et al., *Nucleic Acids Res.* 1990, 18:5433.

Figure 9B:
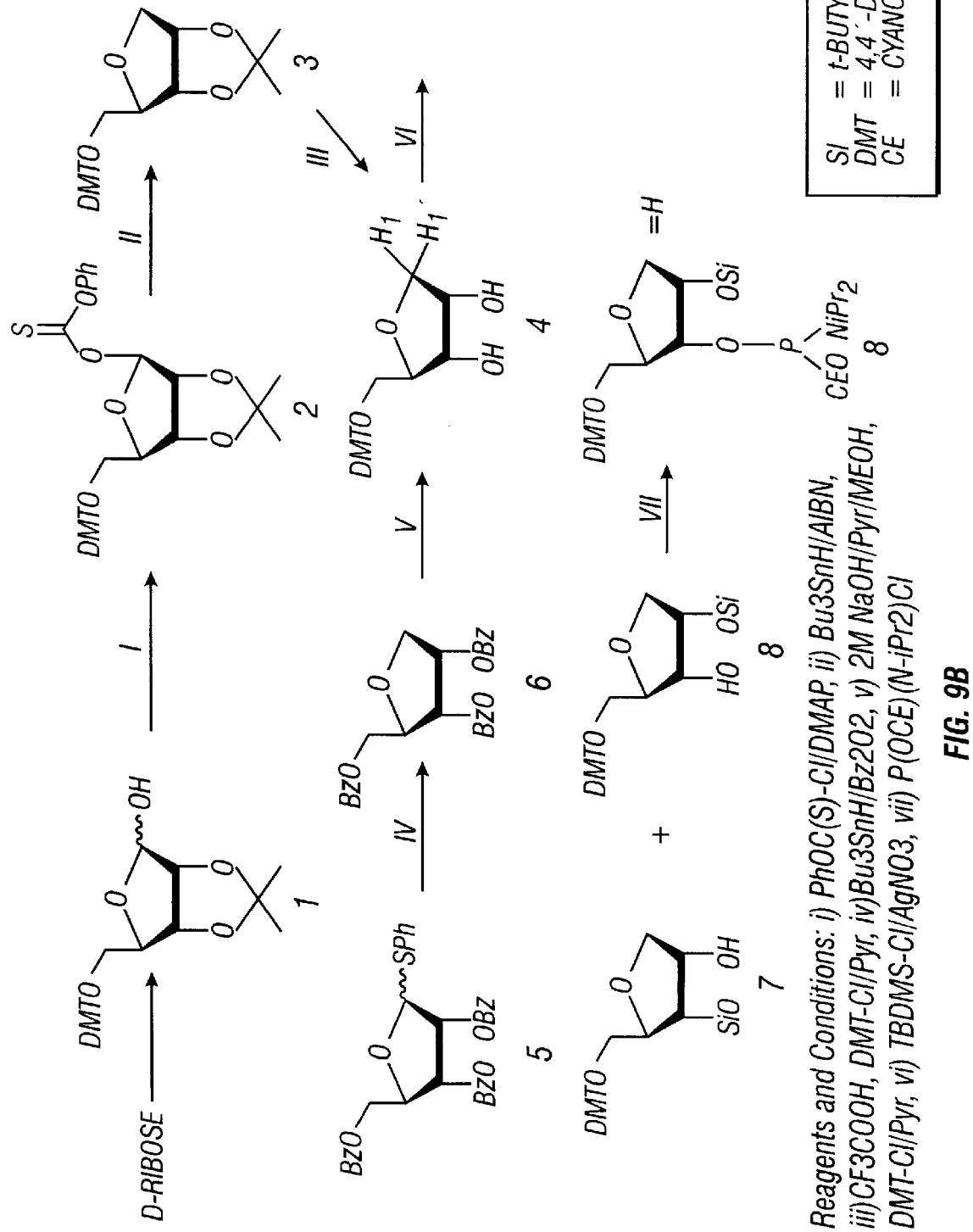

The synthesis of 1-deoxy-D-ribofuranose phosphoramidite 9 is shown in FIG. 9B. Our initial efforts concentrated on the deoxygenation of synthon 1, prepared by a "one pot" procedure from D-ribose. Phenoxythiocarbonylation of acetonide 1 under Robins conditions led to the β-anomer 2 ($J_{1,2}$=1.2 Hz) in modest yield (45–55%). Radical deoxygenation using Bu$_3$SnH/AIBN resulted in the formation of the ribitol derivative 3 in 50% yield. Subsequent deprotection with 90% CF$_3$COOH (10 m) and introduction of a dimethoxytrityl group led to the key intermediate 4 in 40% yield (Yang et al., *Biochemistry* 1992, 31, 5005–5009; Perreault et al., *Biochemistry* 1991, 30, 4020–4025; Paolella et al., *EMBO J.* 1992, 11, 1913–1919; Peiken et al., *Science* 1991, 253, 314–317).

The low overall yield of this (FIG. 9B) route prompted us to investigate a different approach to 4 (FIG. 9B). Phenylthioglycosides, successfully employed in the Keck reaction, appeared to be an alternative. However, it is known that free-radical reduction of the corresponding glycosyl bromides with participating acyl groups at the C2-position can result in the migration of the 2-acyl group to the C1-position (depending on Bu$_3$SnH concentration). Therefore we subjected phenylthioglycoside 5 to radical reduction with Bu$_3$SnH (6.1 eq.) in the presence of Bz$_2$O$_2$ (2 eq.) resulting in the isolation of tribenzoate 6 in 63% yield (FIG. 9B). Subsequent debenzoylation and dimethoxytritylation led to synthon 4 in 70% yield. Introduction of the TBDMS group, using standard conditions, resulted in the formation of a 4:1 ratio of 2- and 3-isomers 8 and 7. The two regioisomers were separated by silica gel chromatography. The 2-O-t-butyldimethylsilyl derivative 8 was phosphitylated to provide phosphoramidite 9 in 82% yield.

Example 6

Referring to FIGS. 10a and 10b the cleavage of substrate is shown by various modified ribozymes compared to unmodified ribozyme at 8 nM and 40 nM concentrations. Specifically, a control ribozyme of sequence ucuccA UCU GAU GAG GCC GAA AGG CCG AAA Auc ccU (where lower case includes a 2' O-methyl group) was compared to ribozyme A (ucu ccA UCU GAU GAG GCC SGG CCG AAA Auc ccu), B (ucu ccA UCU GAU GAG CSG CG AAA Auc ccu), C (ucu ccA UCU GAU GAG GCC bbb bGG CCG AAA Auc ccu), and D (ucu ccA UCU GAU GAG Cbb bbG CGAA AAu ccc u) (where S=hexaethylene glycol linker); and b=abasic nucleotide 4). All were active in cleaving substrate.

Example 7

RNA Cleavage Assay in Vitro

Ribozymes and substrate RNAs were synthesized as described above. Substrate RNA was 5' end-labeled using [γ-$^{32}$P] ATP and T4 polynucleotide kinase (US Biochemicals). Cleavage reactions were carried out under ribozyme "excess" conditions. Trace amount ($\leq$1 nM) of 5' end-labeled substrate and 40 nM unlabeled ribozyme were denatured and renatured separately by heating to 90° C. for 2 min and snap-cooling on ice for 10–15 min. The ribozyme and substrate were incubated, separately, at 37° C. for 10 min in a buffer containing 50 mM Tris-HCl and 10 mM MgCl$_2$. The reaction was initiated by mixing the ribozyme and substrate solutions and incubating at 37° C. Aliquots of 5 μl are taken at regular intervals of time and the reaction quenched by mixing with an equal volume of 2X formamide stop mix. The samples were resolved on 20% denaturing polyacrylamide gels. The results were quantified and percentage of target RNA cleaved is plotted as a function of time.

Referring to FIG. 11 there is shown the general structure of a hammerhead ribozyme targeted against site A (HHA) with various bases numbered. Various substitutions were made at several of the nucleotide positions in HHA. Specifically referring to FIG. 12, substitutions were made at the U4 and U7 positions marked as X4 and X7 and also in loop II in the positions marked by an X. The RNA cleavage activity of these substituted ribozymes is shown in the following figures. Specifically, FIG. 13 shows cleavage by an abasic substituted U4 and an abasic substituted U7. As will be noted, abasic substitution at U4 or U7 does not significantly affect cleavage activity. In addition, inclusion of all abasic moieties in stem II loop does not significantly reduce enzymatic activity as shown in FIG. 14. Further, inclusion of a 3' inverted deoxyribos does not inactivate the RNA cleavage activity as shown in FIG. 15.

Example 8

Smooth Muscle Cell Proliferation Assay

Hammerhead ribozyme (HHB) is targeted to a unique site (site B) within c-myb mRNA. Expression of c-myb protein has been shown to be essential for the proliferation of rat smooth muscle cell (Brown et al., 1992 *J. Biol. Chem.* 267,4625).

The ribozymes that cleaved site B within c-myb RNA described above were assayed for their effect on smooth muscle cell proliferation. Rat vascular smooth muscle cells were isolated and cultured as described (Stnchcomb et al., supra). These primary rat aortic smooth muscle cells (RASMC) were plated in a 24-well plate (5×103 cells/well) and incubated at 37° C. in the presence of Dulbecco's Minimal Essential Media (DMEM) and 10% serum for ~16 hours.

These cells were serum-starved for 48–72 hours in DMEM (containing 0.5% serum) at 37° C. Following serum-starvation, the cells were treated with lipofectamine (LFA)-complexed ribozymes (100 nM ribozyme was complexed with LFA such that LFA:ribozyme charge ration is 4:1).

Ribozyme:LFA complex was incubated with serum-starved RASMC cells for four hours at 37° C. Following the removal of ribozyme:LFA complex from cells (after 4 hours), 10% serum was added to stimulate smooth cell proliferation. Bromo-deoxyuridine (BrdU) was added to stain the cells. The cells were stimulated with serum for 24 hours at 37° C.

Following serum-stimulation, RASMC cells were quenched with hydrogen peroxide (0.3% $H_2O_2$ in methanol) for 30 min at 4° C. The cells were then denatured with 0.5 ml 2N HCl for 20 min at room temperature. Horse serum (0.5 ml) was used to block the cells at 40° C. for 30 min up to ~16 hours.

The RASMC cells were stained first by treating the cells with anti-BrdU (primary) antibody at room temperature for 60 min. The cells were washed with phosphate-buffered saline (PBS) and stained with biotinylated affinity-purified anti-mouse IgM (Pierce, USA) secondary antibody. The cells were counterstained using avidin-biotinylated enzyme complex (ABC) kit (Pierce, USA).

The ratio of proliferating:non-proliferating cells was determined by counting stained cells under a microscope. Proliferating RASMCs will incorporate BrdU and will stain brown. Non-proliferating cells do not incorporate BrdU and will stain purple.

Referring to FIG. 16 there is shown a ribozyme which cleaves the site B referred to as HHB. Substitutions of abasic moieties in place of U4 as shown in FIG. 17 provided active ribozyme as shown in FIG. 18 using the above-noted rat aortic smooth muscle cell proliferation assay.

Administration of Ribozyme

Selected ribozymes can be administered prophylactically, to viral infected patients or to diseased patients, e.g., by exogenous delivery of the ribozyme to a relevant tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal.

The specific delivery route of any selected ribozyme will depend on the use of the ribozyme. Generally, a specific delivery program for each ribozyme will focus on unmodified ribozyme uptake with regard to intracellular localization, followed by demonstration of efficacy. Alternatively, delivery to these same cells in an organ or tissue of an animal can be pursued. Uptake studies will include uptake assays to evaluate cellular ribozyme uptake, regardless of the delivery vehicle or strategy. Such assays will also determine the intracellular localization of the ribozyme following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:

a. encapsulation in liposomes, b. transduction by retroviral vectors, c. conjugation with cholesterol, d. localization to nuclear compartment utilizing antigen binding or nuclear targeting site found on most snRNAs or nuclear proteins, e. neutralization of charge of ribozyme by using nucleotide derivatives, and f. use of blood stem cells to distribute ribozymes throughout the body.

Delivery strategies useful in the present invention, include: ribozyme modifications, and particle carrier drug delivery vehicles. Unmodified ribozymes, like most small molecules, are taken up by cells, albeit slowly. To enhance cellular uptake, the ribozyme may be modified essentially at random, in ways which reduce its charge but maintains specific functional groups. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Use

Those in the art will recognize that these ribozymes can be used in place of other enzymatic RNA molecules for both in vitro and in vivo uses well known in the art. See Draper WO 93/23569 and Sullivan WO 94/12516.

Chemical modifications of the phosphate backbone will reduce the negative charge allowing free diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein. In another study, an antibody targeted liposome delivery system containing an RNA molecule 3,500 nucleotides in length and antisense to a structural protein of HIV, inhibited virus proliferation in a sequence specific manner. Not only did the antibody target the liposomes to the infected cells, but it also triggered the internalization of the liposomes by the infected cells. Triggering the endocytosis is useful for viral inhibition. Finally, liposome delivered synthetic ribozymes have been shown to concentrate in the nucleus of H9 (an example of an HIV-sensitive cell) cells and are functional as evidenced by their intracellular cleavage of the sequence. Liposome delivery to other cell types using smaller ribozymes (less than 142 nucleotides in length) exhibit different intracellular localizations.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systematically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell. This method is particularly useful for treating AIDS using anti-HIV ribozymes.

Also preferred in AIDS therapy is the use of a liposome formulation which can deliver oligonucleotides to lymphocytes and macrophages. This oligonucleotide delivery system inhibits HIV proliferation in infected primary immune cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration. This formulation offers an excellent delivery vehicle for anti-AIDS ribozymes for two reasons. First, T-helper lymphocytes and macrophages are the primary cells infected by the virus, and second, a subcutaneous administration delivers the ribozymes to the resident HIV-infected lymphocytes and macrophages in the lymph node. The liposomes then exit the lymphatic system, enter the circulation, and accumulate in the spleen, where the ribozyme is delivered to the resident lymphocytes and macrophages.

Intraperitoneal administration also leads to entry into the circulation, with once again, the molecular weight or size of the ribozyme-delivery vehicle complex controlling the rate of entry.

Liposomes injected intravenously show accumulation in the liver, lung and spleen. The composition and size can be adjusted so that this accumulation represents 30% to 40% of the injected dose. The remaining dose circulates in the blood stream for up to 24 hours.

The chosen method of delivery should result in cytoplasmic accumulation in the afflicted cells and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogues may require different dosaging. Descriptions of useful systems are provided in the art cited above, all of which is hereby incorporated by reference herein.

For a more detailed description of ribozyme design, see, Draper, U.S. Ser. No. 08/103,243 filed Aug. 6, 1993, hereby incorporated by reference herein in its entirety.

Other embodiments are within the following claims.

What is claimed is:

1. A nucleic acid molecule comprising an abasic moiety at the 3' end or at the 5' end or at both the 3' end and the 5' end of said nucleic acid molecule, wherein said abasic moiety lacks a nucleic acid base.

2. The nucleic acid molecule of claim 1, wherein said abasic moiety is an inverted abasic moiety.

3. The nucleic acid molecule of any of claims 1–2, wherein said abasic moiety comprises a sugar modification.

4. The nucleic acid molecule of claim 3, wherein said sugar modification is 2'-H.

5. The nucleic acid molecule of claim 3, wherein said sugar modification is 2'-O-methyl.

6. The nucleic acid molecule of any of claims 1–2, wherein said nucleic acid molecule is an enzymatic nucleic acid molecule.

7. The nucleic acid molecule of any of claims 1–2, wherein said nucleic acid molecule is an antisense nucleic acid molecule.

8. The nucleic acid molecule of any of claims 1–2, wherein said abasic moiety is present at the 3' end of the nucleic acid molecule.

9. The nucleic acid molecule of any of claims 1–2, wherein said abasic moiety is present at the 5' end of the nucleic acid molecule.

10. The nucleic acid molecule of any of claims 1–2, wherein said abasic nucleic acid moiety is present at the 3' end and the 5' end of said nucleic acid molecule.

11. A cell including the nucleic acid molecule of any of claims 1–2.

12. The cell of claim 11, wherein said cell is a mammalian cell.

13. The cell of claim 12, wherein said mammalian cell is a human cell.

* * * * *

SEQUENCE LISTING (1) GENERAL INFORMATION:

(iii) NUMBER OF SEQUENCES:      21

(2) INFORMATION FOR SEQ ID NO: 1:

(i) SEQUENCE CHARACTERISTICS:
       (A) LENGTH:         36 base pairs
       (B) TYPE:           nucleic acid
       (C) STRANDEDNESS:   single
       (D) TOPOLOGY:       linear (xi) SEQUENCE DESCRIPTION: SEQ ID NO: 1:

UCUCCAUCUG AUGAGGCCGA AAGGCCGAAA AUCCCU                          36

(2) INFORMATION FOR SEQ ID NO: 2:

(i) SEQUENCE CHARACTERISTICS:
       (A) LENGTH:         33 base pairs
       (B) TYPE:           nucleic acid
       (C) STRANDEDNESS:   single
       (D) TOPOLOGY:       linear (ix) FEATURE:
       (D) OTHER INFORMATION:   The letter "N" stands for
           hexaethylene glycol linker.

(xi) SEQUENCE DESCRIPTION: SEQ ID NO: 2:

UCUCCAUCUG AUGAGGCCNG GCCGAAAAUC CCU                             33

(2) INFORMATION FOR SEQ ID NO: 3:

(i) SEQUENCE CHARACTERISTICS:
       (A) LENGTH:         29 base pairs
       (B) TYPE:           nucleic acid
       (C) STRANDEDNESS:   single
       (D) TOPOLOGY:       linear (ix) FEATURE:
       (D) OTHER INFORMATION:   The letter "N" stands for
           hexaethylene glycol linker.

(xi) SEQUENCE DESCRIPTION: SEQ ID NO: 3:

UCUCCAUCUG AUGAGCNGCG AAAAUCCCU                                  29

(2) INFORMATION FOR SEQ ID NO: 4:

(i) SEQUENCE CHARACTERISTICS:
       (A) LENGTH:         36 base pairs
       (B) TYPE:           nucleic acid
       (C) STRANDEDNESS:   single
       (D) TOPOLOGY:       linear (ix) FEATURE:
       (D) OTHER INFORMATION:   The letter "N" stands for
           abasic nucleotide 4.

(xi) SEQUENCE DESCRIPTION: SEQ ID NO: 4:

UCUCCAUCUG AUGAGGCCNN NNGGCCGAAA AUCCCU                          36

(2) INFORMATION FOR SEQ ID NO: 5:

(i) SEQUENCE CHARACTERISTICS:
       (A) LENGTH:         32 base pairs
       (B) TYPE:           nucleic acid
       (C) STRANDEDNESS:   single
       (D) TOPOLOGY:       linear

```
        (ix) FEATURE:
             (D) OTHER INFORMATION:   The letter "N" stands for
                 abasic nucleotide 4.

(xi) SEQUENCE DESCRIPTION: SEQ ID NO: 5:

UCUCCAUCUG AUGAGCNNNN GCGAAAAUCC CU                                           32

(2) INFORMATION FOR SEQ ID NO: 6:

(i) SEQUENCE CHARACTERISTICS:
            (A) LENGTH:              11 base pairs
            (B) TYPE:                nucleic acid
            (C) STRANDEDNESS:        single
            (D) TOPOLOGY:            linear (ix) FEATURE:
             (D) OTHER INFORMATION:   The letter "N" stands for any base.
                 The letter "H" stands for C, A or U.

(xi) SEQUENCE DESCRIPTION: SEQ ID NO: 6:

NNNNUHNNNN N                                                                 11

(2) INFORMATION FOR SEQ ID NO: 7:

(i) SEQUENCE CHARACTERISTICS:
            (A) LENGTH:              28 base pairs
            (B) TYPE:                nucleic acid
            (C) STRANDEDNESS:        single
            (D) TOPOLOGY:            linear (ix) FEATURE:
             (D) OTHER INFORMATION:   The letter "N" stands for any base.

(xi) SEQUENCE DESCRIPTION: SEQ ID NO: 7:
             NNNNNCUGAN GAGNNNNNNC GAAANNNN                                  28

(2) INFORMATION FOR SEQ ID NO: 8:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (ix) FEATURE:
             (D) OTHER INFORMATION:   The letter "N" stands for any base.
                 The letter "Y" stands for U or C.
                 The letter "H" stands for A, U or C.

(xi) SEQUENCE DESCRIPTION: SEQ ID NO: 8:

NNNNNNNYNG HYNNN                                                             15

(2) INFORMATION FOR SEQ ID NO: 9:

(i) SEQUENCE CHARACTERISTICS:
            (A) LENGTH:              47 base pairs
            (B) TYPE:                nucleic acid
            (C) STRANDEDNESS:        single
            (D) TOPOLOGY:            linear (ix) FEATURE:
             (D) OTHER INFORMATION:   The letter "N" stands for any base.

(xi) SEQUENCE DESCRIPTION: SEQ ID NO: 9:

NNNNGAAGNN NNNNNNNNNA AAHANNNNNN NACAUUACNN NNNNNNN                          47

(2) INFORMATION FOR SEQ ID NO: 10:

(i) SEQUENCE CHARACTERISTICS:
            (A) LENGTH:              85 base pairs
```

```
            (B) TYPE:                nucleic acid
            (C) STRANDEDNESS:        single
            (D) TOPOLOGY:            linear (xi) SEQUENCE DESCRIPTION: SEQ ID NO: 10:

UGGCCGGCAU GGUCCCAGCC UCCUCGCUGG CGCCGGCUGG GCAACAUUCC GAGGGGACCG    60

UCCCCUCGGU AAUGGCGAAU GGGAC                                         85

(2) INFORMATION FOR SEQ ID NO: 11:

(i) SEQUENCE CHARACTERISTICS:
            (A) LENGTH:              176 base pairs
            (B) TYPE:                nucleic acid
            (C) STRANDEDNESS:        single
            (D) TOPOLOGY:            linear (xi) SEQUENCE DESCRIPTION: SEQ ID NO: 11:

GGGAAAGCUU GCGAAGGGCG UCGUCGCCCC GAGCGGUAGU AAGCAGGGAA CUCACCUCCA    60

AUUUCAGUAC UGAAAUUGUC GUAGCAGUUG ACUACUGUUA UGUGAUUGGU AGAGGCUAAG   120

UGACGGUAUU GGCGUAAGUC AGUAUUGCAG CACAGCACAA GCCCGCUUGC GAGAAU       176

(2) INFORMATION FOR SEQ ID NO: 12:

(i) SEQUENCE CHARACTERISTICS:
            (A) LENGTH:              13 base pairs
            (B) TYPE:                nucleic acid
            (C) STRANDEDNESS:        single
            (D) TOPOLOGY:            linear (xi) SEQUENCE DESCRIPTION: SEQ ID NO: 12:

GACCGUCAGA CGC                                                      13

(2) INFORMATION FOR SEQ ID NO: 13:

(i) SEQUENCE CHARACTERISTICS:
            (A) LENGTH:              32 base pairs
            (B) TYPE:                nucleic acid
            (C) STRANDEDNESS:        single
            (D) TOPOLOGY:            linear (xi) SEQUENCE DESCRIPTION: SEQ ID NO: 13:

GCUGGUCUGA UGAGGUCCGG ACCGAAACGG UC                                 32

(2) INFORMATION FOR SEQ ID NO: 14:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 14:

AGGGAUUAAU GGAGA                                                    15

(2) INFORMATION FOR SEQ ID NO: 15:

(i) SEQUENCE CHARACTERISTICS:
            (A) LENGTH:              32 base pairs
            (B) TYPE:                nucleic acid
            (C) STRANDEDNESS:        single
            (D) TOPOLOGY:            linear (xi) SEQUENCE DESCRIPTION: SEQ ID NO: 15:

UCUCCAUCUG AUGAGGGAAA CCGAAAAUCC CU                                 32
```

(2) INFORMATION FOR SEQ ID NO: 16:

(i) SEQUENCE CHARACTERISTICS:
        (A) LENGTH:           15 base pairs
        (B) TYPE:             nucleic acid
        (C) STRANDEDNESS:    single
        (D) TOPOLOGY:        linear (xi) SEQUENCE DESCRIPTION: SEQ ID NO: 16:

AGGGAUUAAU GGAGA                                                    15

(2) INFORMATION FOR SEQ ID NO: 17:

(i) SEQUENCE CHARACTERISTICS:
        (A) LENGTH:           33 base pairs
        (B) TYPE:             nucleic acid
        (C) STRANDEDNESS:    single
        (D) TOPOLOGY:        linear (ix) FEATURE:
        (D) OTHER INFORMATION: The letter "N" stands for
            abasic substitutions.

(xi) SEQUENCE DESCRIPTION: SEQ ID NO: 17:

UCUCCAUCNG ANGAGGNNNN CCGAAAAUCC CUN                          33

(2) INFORMATION FOR SEQ ID NO: 18:

(i) SEQUENCE CHARACTERISTICS:
        (A) LENGTH:           15 base pairs
        (B) TYPE:             nucleic acid
        (C) STRANDEDNESS:    single
        (D) TOPOLOGY:        linear (xi) SEQUENCE DESCRIPTION: SEQ ID NO: 18:

GGAGAAUUGG AAAAC                                                    15

(2) INFORMATION FOR SEQ ID NO: 19:

(i) SEQUENCE CHARACTERISTICS:
        (A) LENGTH:           34 base pairs
        (B) TYPE:             nucleic acid
        (C) STRANDEDNESS:    single
        (D) TOPOLOGY:        linear (xi) SEQUENCE DESCRIPTION: SEQ ID NO: 19:

GUUUUCCCUG AUGAGGGGAA ACCCGAAAUU CUCC                         34

(2) INFORMATION FOR SEQ ID NO: 20:

(i) SEQUENCE CHARACTERISTICS:
        (A) LENGTH:           15 base pairs
        (B) TYPE:             nucleic acid
        (C) STRANDEDNESS:    single
        (D) TOPOLOGY:        linear (xi) SEQUENCE DESCRIPTION: SEQ ID NO: 20:

GGAGAAUUGG AAAAC                                                    15

(2) INFORMATION FOR SEQ ID NO: 21:

(i) SEQUENCE CHARACTERISTICS:
        (A) LENGTH:           34 base pairs
        (B) TYPE:             nucleic acid
        (C) STRANDEDNESS:    single
        (D) TOPOLOGY:        linear (ix) FEATURE:

-continued (D) OTHER INFORMATION: The letter "N" stands for
    abasic substitutions.

(xi) SEQUENCE DESCRIPTION: SEQ ID NO: 21:

GUUUUCCCNG AUGAGGGGAA ACCCGAAAUU CUCC                    34